(12) United States Patent
Shastri et al.

(10) Patent No.: US 12,030,963 B2
(45) Date of Patent: *Jul. 9, 2024

(54) MATRICES COMPRISING A MODIFIED POLYSACCHARIDE

(71) Applicant: Albert-Ludwigs-Universität Freiburg, Freiburg (DE)

(72) Inventors: V. Prasad Shastri, Nashville, TN (US); Aurélien Forget, Freiburg (DE)

(73) Assignee: MAPTech Holdings UG, Breisach (DE)

( * ) Notice: Subject to any disclaimer, the term of this patent is extended or adjusted under 35 U.S.C. 154(b) by 370 days.

This patent is subject to a terminal disclaimer.

(21) Appl. No.: 17/198,081

(22) Filed: Mar. 10, 2021

(65) Prior Publication Data
US 2021/0355247 A1  Nov. 18, 2021

Related U.S. Application Data

(63) Continuation of application No. 16/000,370, filed on Jun. 5, 2018, now Pat. No. 10,968,285, which is a continuation of application No. 14/239,200, filed as application No. PCT/EP2012/003504 on Aug. 17, 2012, now abandoned.

(60) Provisional application No. 61/524,782, filed on Aug. 18, 2011.

(30) Foreign Application Priority Data

Aug. 18, 2011 (EP) .................................. 11177886

(51) Int. Cl.
| | |
|---|---|
| A61K 31/715 | (2006.01) |
| A61K 8/73 | (2006.01) |
| A61K 47/36 | (2006.01) |
| A61L 31/12 | (2006.01) |
| A61Q 90/00 | (2009.01) |
| C08B 37/00 | (2006.01) |
| C08B 37/08 | (2006.01) |
| C08H 1/00 | (2006.01) |
| C08L 5/00 | (2006.01) |
| C08L 5/12 | (2006.01) |
| C10M 107/36 | (2006.01) |
| C12N 5/00 | (2006.01) |

(52) U.S. Cl.
CPC .............. *C08B 37/006* (2013.01); *A61K 8/73* (2013.01); *A61K 31/715* (2013.01); *A61K 47/36* (2013.01); *A61L 31/125* (2013.01); *A61Q 90/00* (2013.01); *C08B 37/00* (2013.01); *C08B 37/003* (2013.01); *C08B 37/0039* (2013.01); *C08B 37/0042* (2013.01); *C08B 37/0063* (2013.01); *C08B 37/0069* (2013.01); *C08B 37/0072* (2013.01); *C08B 37/0075* (2013.01); *C08H 1/00* (2013.01); *C08L 5/00* (2013.01); *C08L 5/12* (2013.01); *C10M 107/36* (2013.01); *C12N 5/0068* (2013.01); *C12N 2533/50* (2013.01); *C12N 2533/70* (2013.01)

(58) Field of Classification Search
CPC .............................. A61K 31/715; A61K 47/36
See application file for complete search history.

(56) References Cited

U.S. PATENT DOCUMENTS

| | | |
|---|---|---|
| 10,968,285 B2 | 4/2021 | Shastri et al. |
| 11,407,978 B2 | 8/2022 | Shastri et al. |
| 2004/0235027 A1* | 11/2004 | Lam ........................ C40B 50/18 435/7.1 |
| 2014/0314722 A1 | 10/2014 | Shastri et al. |
| 2022/0411756 A1 | 12/2022 | Shastri et al. |

FOREIGN PATENT DOCUMENTS

| | | |
|---|---|---|
| WO | WO 02/18448 A2 | 3/2002 |
| WO | WO 03/074087 A1 | 9/2003 |

OTHER PUBLICATIONS

Forget et al., (2013) Polysacchatride hydrogels with tunable stiffness and provasculogenic properties via α-helix to β-sheet switch in secondary structure. PNAS, 110(32), 12887-12892 (Year: 2013).*
Fernández-Cossío et al., (2007), Biocompatibility of agarose gel as a dermal filler: Histological evaluation of subcutaneous implants. Plastic and Reconstructive Surgery, 120(5) 1161-1169. (Year: 2007).*
International Search Report and Written Opinion dated Mar. 22, 2013 for Application No. PCT/EP2012/003504.
International Preliminary Report on Patentability dated Feb. 27, 2014 for Application No. PCT/EP2012/003504.
Afanassiev et al. Preparation of DNA and protein micro arrays on glass slides coated with an agarose film. Nucleic Acids Res. Jun. 15, 2000;28(12):E66.
Bragd et al. Selective oxidation of carbohydrates by 4-AcNH-TEMPO/peracid systems. Carbohydrate Polymers. 2002. 49(4), 397-406.
Bragd et al. TEMPO-Mediated Oxidation of Polysaccharides: Survey of Methods and Applications. Topics in Catalysis 27, 49-66 (2004).
Cao et al.. Photoimmobilization of biomolecules within a 3-dimensional hydrogel matrix. J Biomater Sci Polym Ed. 2002;13(6):623-36.
Forget et al. Polysaccharide hydrogels with tunable stiffness and provasculogenic properties via α-helix to β-sheet switch in secondary structure. Proc Natl Acad Sci U S A. Aug. 6, 2013;110(32):12887-92. doi: 10.1073/pnas.1222880110. Epub Jul. 25, 2013.
Hassan et al. Acid-catalyzed oxidation of some sulfated polysaccharides: Kinetics and mechanism of oxidation of kappa-carrageenan by cerium(IV) in aqueous perchlorate solutions. J. Molecular Catalysis A: Chemical. Nov. 1, 2010. 332(1-2), 138-44.

(Continued)

*Primary Examiner* — Kara D Johnson
(74) *Attorney, Agent, or Firm* — Wolf, Greenfield & Sacks, P.C.

(57) ABSTRACT

The present invention discloses a matrix comprising a modified polysaccharide consisting of repeating disaccharide units whereby in at least 11% of the disaccharide units one primary alcohol group is oxidized into a carboxylic acid group.

10 Claims, 18 Drawing Sheets

Specification includes a Sequence Listing.

(56) References Cited

OTHER PUBLICATIONS

Luo et al. A photolabile hydrogel for guided three-dimensional cell growth and migration. Nat Mater. Apr. 2004;3(4):249-53. doi: 10.1038/nmat1092. Epub Mar. 21, 2004.
Muzzarelli et al. 6-Oxychitins, novel hyaluronan-like regiospecifically carboxylated chitins. Carbohydrate Polymers, App Sci Publishers, Ltd. Aug. 1, 1999: 39(4), 361-7.
Ogawa et al. Three D structures of chitosan. Int J Biol Macromol. Apr. 2004;34(1-2):1-8.
Padmanabhan et al. A preliminary investigation of modified alginates as a matrix for gene transfection in a HeLa cell model. Pharm Dev Technol. Jan. 2002;7(1):97-101.
Rowley et al. Alginate hydrogels as synthetic extracellular matrix materials. Biomaterials. Jan. 1999;20(1):45-53.
Tan et al. Injectable, Biodegradable Hydrogels for Tissue Engineering Applications. Materials (Basel). Mar. 10, 2010;3(3):1746-67 . . . .

* cited by examiner

C1
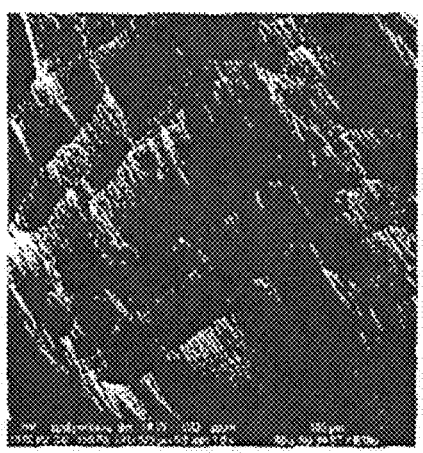
D1
C2
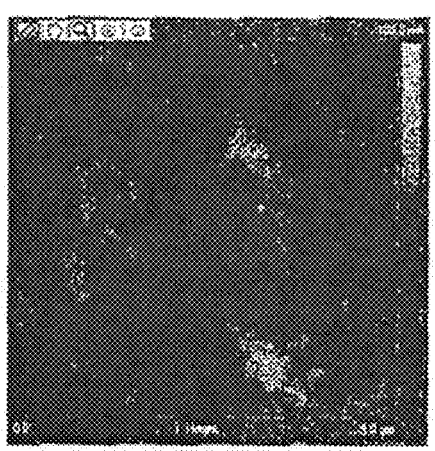
D2
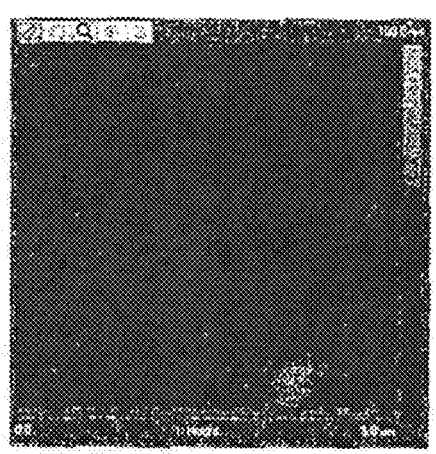
C3
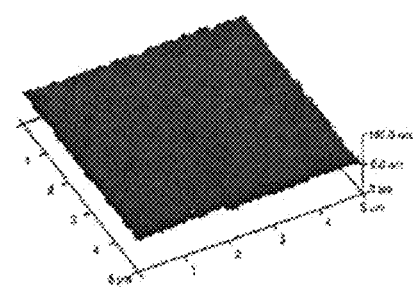
D3
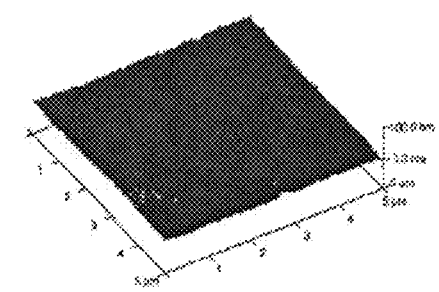
Figure 8C
Figure 8D

MATRICES COMPRISING A MODIFIED POLYSACCHARIDE

CROSS-REFERENCE TO RELATED APPLICATIONS

This application is a continuation of U.S. patent application Ser. No. 16/000,370, filed Jun. 5, 2018, entitled "Matrices Comprising a Modified Polysaccharide," which is a continuation of U.S. patent application Ser. No. 14/239,200, filed Jul. 2, 2014, entitled "Matrices Comprising a Modified Polysaccharide," which is a national stage filing under 35 U.S.C. § 371 of International Patent Application Serial No. PCT/EP2012/003504, filed Aug. 17, 2012, entitled "Matrices Comprising a Modified Polysaccharide," which claims the benefit of U.S. Provisional Patent Application Ser. No. 61/524,782, filed Aug. 18, 2011, entitled "Extracellular Matrices which Can Be Used as Scaffold for Living Cells," and to European Patent Application No. 11177886.6, filed Aug. 18, 2011, entitled "Matrices Comprising a Modified Polysaccharide, each of which is incorporated herein by reference in its entirety.

Reference to an Electronic Sequence Listing

The contents of the electronic sequence listing (F087370001US00-SEQ-TC.txt; Size: 960 bytes; and Date of Creation: May 18, 2021) is herein incorporated by reference in its entirety.

FIELD OF THE INVENTION

The present invention relates to matrices comprising a modified polysaccharide and the applications of such matrices. The matrixes can be used as scaffold for living cells regenerative implants, plastic surgery implants and controlled drug release implants. In addition thereto, the matrixes of the present invention are suitable for use as a food additive, a component for cosmetic compositions and for other industrial purposes.

BACKGROUND OF THE PRESENT INVENTION

In the text of the present application, the nomenclature of amino acids and of peptides is used according to "Nomenclature and symbolism for amino acids and peptides", Pure & Appl. Chem., Vol. 56, No. 5, pp. 595-624, 1984, if not otherwise stated.

The following abbreviations have the meaning as given in the following list, if not otherwise stated:
AFM atomic force microscopy
CD circular dichroism
CSF cell shape factor
CT computed tomography
DIC differential interference contrast imaging
DLS dynamic light scattering
DMEM Dulbecco's modified Eagle's medium
DNA deoxyribonucleic acid
ECM extracellular matrix
EDC 1-(3-dimethylaminopropyl)-3-ethylcarbodiimide hydrochloride
ESEM environmental scanning electron microscopy
FTIR Fourier transform infrared spectroscopy
HCl hydrochloric acid
KBr potassium bromide
MAS-NMR magic angle spinning NMR
MD molecular dynamics
MES 2-(N-morpholino)ethanesulfonic acid
Mn number average molecular weight
MRI magnetic resonance imaging
MWCO molecular weight cut off
NaOCl sodium hypochloride
NaOH sodium hydroxide
NMR nuclear magnetic resonance
PCR polymerase chain reaction
PDB protein database
RNA ribonucleic acid
RMSD root mean square deviation
SEM scanning electron microscopy
siRNA small interfering RNA
SLS static light scattering
TEMPO (2,2,6,6-tetramethyl-piperidin-1-yl)oxyl.

Living cells of higher organisms reside in an environment that is mechanically and biologically well-defined by an extracellular matrix (in the following ECM). Structural and mechanical aspects of the ECM such as stiffness and topography can have a substantial influence on different cell functions like cell growth or differentiation of the cells.

The present invention provides matrices wherein important mechanical and chemical properties of the matrix can be adjusted according to the desired application. Thus, it can be for example required to lower the shear modulus G' of the matrix or to improve the optical properties towards an increased transparency of the matrix.

The cell surrounding has been considered in the past decades to be an important piece of the puzzle of organogenesis. It is known that each type of cell builds and evolves in a specific environment that provides the mechanical properties and the nutritional needs of the cell. This environment is called extracellular matrix (ECM). Structural and functional components of the ECM can modulate cell behavior and function and also determine which cell can interact with another in the human body. Nevertheless, most of these intercellular interactions are not fully understood. It has been shown that the properties of the ECM supporting the cell in the human body have many aspects (physical and chemical) that have been shown to impact the cell fate in vitro and in vivo. It has been found that in addition to cell adhesion moieties and growth factors, the physical attributes of a cellular microenvironment namely, stiffness and topography are another important element in dictating and controlling cell fate and function.

Providing a synthetic ECM would be a significant contribution to investigation of such intercellular interaction. Importantly, a model employing such ECM would allow mimicking of human tissues in vitro and be amenable to translation in vivo. A further aim of this model is to enable communicating with the body and aid in healing or regeneration of tissues. Injectable, biologically well-defined matrixes with tailor-made and tunable physical properties would be the evolutionary next-step in synthetic niches for cells.

The present invention provides a matrix suitable for these applications. Moreover, the matrix of the present invention can also be used as a food additive, material for surgery implants and controlled drug release implants, as lubricant for industrial purposes as well as for conditioning of liquids.

In the present application the matrix is defined as molecules composing the cell surrounding. In general matrix is made up of different components that can be classified as:
(1) the soluble molecules, e.g. growth factor and other signaling molecules and
(2) the structural polymers, composed of proteins and polysaccharides that determines the mechanical properties of the tissues.

The term "growth factor" relates to a naturally occurring compound which is capable of stimulating cellular growth, proliferation and differentiation. Preferably, the growth fact is a polypeptide or a protein, for instance, a water-soluble protein.

The term "protein" relates to a polymeric structure which consists of one or several polypeptides. Polypeptides, in turn, consist of amino acid residues joined together by peptide bonds. Preferably, the amino acids of the proteins are L-α-amino acids, whereby proteinogenic amino acids are particularly preferred. It is preferred that proteins acting as components of an extracellular matrix are not water-soluble. The term "peptide sequence" used in the present invention relates to a polypeptide. Preferably, a peptide sequence has between 2 and 50 amino acid residues, particularly preferred between 5 and 20 amino acid residues.

In the present application the term "polysaccharide" relates to a polymeric carbohydrate structure which is formed of repeating units joined together by glycosidic bonds. Preferably, the repeating units are either mono- or disaccharides and the polymeric structure of the polysaccharide is non-branched. It is preferred that the number average molecular weight of the polysaccharide ranges from 10 000 Da to 500 000 Da, particularly preferred the number average molecular weight of the polysaccharide ranges from 50 000 Da to 300 000 Da, whereby the number average molecular weight of the polysaccharide ranging from 80 000 Da to 140 000 Da is even more preferred.

Some synthetic matrixes for use as ECM have already been commercialized. So far three different strategies have been explored to produce synthetic ECMs:
(1) Use of animal protein extracts such as Matrigel® which suffer from a lack of batch to batch reproducibility and a poor definition of the components. This leads to difficulties in the interpretation of the results obtained with such ECMs.
(2) Use of synthetic polymers such as degradable polyester that although biocompatible are not easy to synthesize and manufacture and additionally, require knowledge in synthetic chemistry to set it up and are also difficult to translate into in vivo clinical settings.
(3) Use of natural components of the ECM such as collagen or hyaluronic acid, which reproduce only one aspect of the natural ECM environment.

As outlined in the review of Tan et al (*Materials* 2010, 3, 1746-1767) various polysaccharides have been suggested as suitable materials for ECMs in the last decades. Prominent among them are hyaluronic acid, alginate acid and chitosan. Hyaluronic acid when modified using long chain alcohols can yield gels that are formed due to physical cross-links established by the aggregations of the hydrophobic alkyl chains in water. Hyaluronic acid can also be gelled using covalent crosslinking. In this case, the hyaluronic acid is oxidized to bear aldehyde groups which are then reacted with N-succinyl modified chitosan or other biopolymers. Subsequently, the crosslinking is induced by diamine through Schiff base formation. Alginic acid can also be processed into gels that can serve as cell supports by ionic crosslinking it with divalent cations $Ca^{2+}$, $Mg^{2+}$, $Ba^{2+}$ or $Sr^{2+}$.

SUMMARY OF THE INVENTION

The present invention relates to a matrix comprising a modified polysaccharide consisting of repeating disaccharide units whereby in at least 11% of the disaccharide units one primary alcohol group is oxidized into a carboxylic acid.

It is an essential component of the matrix of the present invention to contain at least one modified polysaccharide whereby the modified polysaccharide consists of repeating disaccharide units. In a preferred embodiment the modified polysaccharide is derived from agarose. In yet another preferred embodiment the modified polysaccharide is derived from fragmented agarose.

Agar, the main source of agarose is a structural polysaccharide of the cell walls of a variety of red algae. Important sources of agar are Gelidiaceae such as *Gelidium amansii, Gelidium japonicum, Gelidium pacificum, Gelidium subcostatum, Pterocladia tenuis* and *Acanthopeltis japonica*, red algae belonging to Gracilariaceae such as *Gracilaria verrucosa* and *Gracilaria gigas*, red algae belonging to Ceramiaceae such as *Ceramium kondoi* and *Campylaephora hypnaeoides*. Agar consists of two groups of polysaccharides, namely agarose and agaropectin. Agarose is a neutral, linear polysaccharide with no branching and has a backbone consisting of 1,3-linked β-D-galactose-(1-4)-α-L-3,6 anhydrogalactose repeating units. This dimeric repeating unit, called agarobiose differs from a similar dimeric repeating unit called carrabiose which is derived from carrageenan in that it contains 3,6-anhydrogalactose in the L-form and does not contain sulfate groups.

Such dimeric repeating units derived from naturally occurring polysaccharides are chemically modified by the regioselective oxidation of the primary alcohol group to a carboxylic acid group. Such oxidation can conveniently carried out by sodium hypochloride in the presence of 2,2,6,6-Tetramethylpiperidine-1-oxyl (TEMPO). The reaction mechanism is shown in Scheme 1 below. It goes without saying that the regioselective oxidation of the primary alcohol group to the carboxylic acid group can be also performed by other reactions which are well-known to a person skilled in the art as long as these reactions are sufficiently selective and no undesired oxidation of the secondary alcohol group and of other functionalities of the polysaccharides takes place. In addition, the oxidation of the primary alcohol groups of the polysaccharide can also be carried out by an enzymatic process or upon using a bacteriological system.

Scheme 1

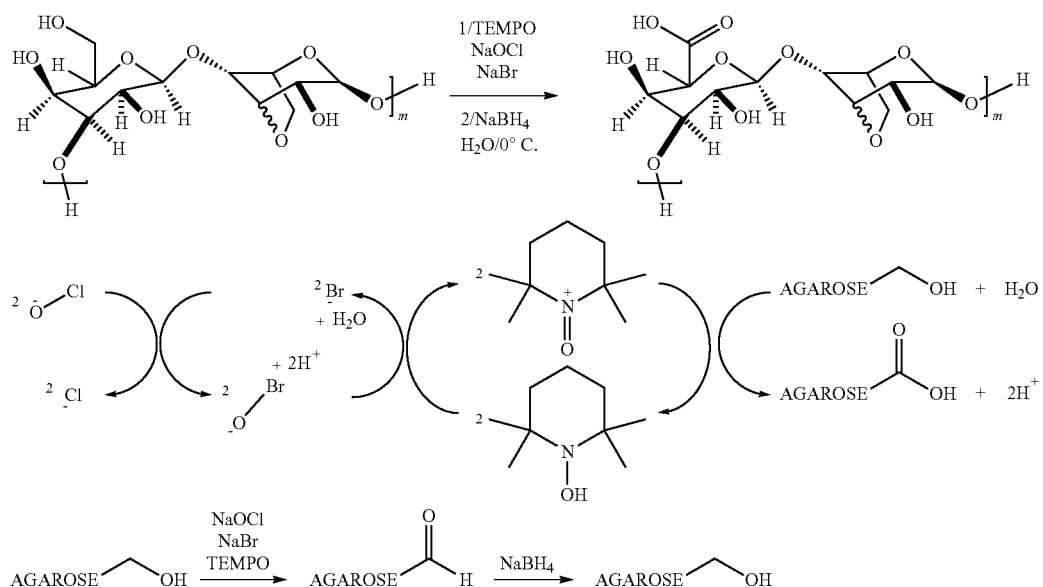

Depending on the chosen reaction conditions it is possible to oxidize only a certain percentage of the primary alcohol groups of the polysaccharide. According to the invention at least 11% of the disaccharide repeat units are oxidized. In a preferred embodiment at least 20 up to 99% of the disaccharide repeat units of the primary alcohol groups are oxidized into the carboxylic acid group. In a particularly preferred embodiment in 50-95% of the disaccharide repeat units the primary alcohol group is oxidized into the carboxylic acid group. In yet another embodiment more than 75% of the disaccharide repeat units the primary alcohol group is oxidized to the carboxylic acid group.

Thus, the oxidation reaction is carried out in a controlled manner so that only a partial oxidation of the primary alcohol groups takes place. However, the polysaccharide can also be oxidized in such a way that about 100% of the primary alcohol groups are oxidized.

The completely or partially oxidized polysaccharide can be subsequently blended with an unmodified polysaccharide which may either be the same polysaccharide or another polysaccharide. Since the nature and extend of the chemical modification of the modified polysaccharide can be precisely controlled and the blending ratio with another polysaccharide or the same unmodified polysaccharide can be adjusted it is possible to control the chemical properties of the resulting matrix.

The weight ratio of the modified polysaccharide in the matrix of the present invention is in the range of 1-99 wt.-%. In a preferred embodiment the present invention the weight ratio of the modified polysaccharide in the matrix is greater than 1 wt.-%, preferably it is greater than 10 wt.-%. It is yet even more preferred that the ratio of the modified polysaccharide in the matrix is greater than 20 wt. %, in particular greater than 50 wt.-%.

One important aspect of the present invention is the shear modulus G' of the matrix. According to the present invention the shear modulus can range from about 10 Pa which reflects the structure of a nerve tissue to about $10^7$ Pa which corresponds with the shear modulus of cartilage tissues. By blending gels of different extent of chemical modification the nanoscale structure of the gel can be impacted. It has been shown that nanoscale topography influences cell shape, cytoskeletal assembly and function. It is for this reason that the matrix of the present invention can induce changes in mammalian cell shape or mammalian cell function.

The shear modulus of the matrix ranges preferably from 1 Pa to 100 kPa, more preferred from 1 Pa to 50 kPa and in a most preferred embodiment in a range from 10 Pa to 10 kPa, whereby the measurement of the shear modulus is carried out at a temperature of 37° C. as specified below.

In an especially preferred embodiment agarose wherein the primary alcohol group has been oxidized in a carboxylic acid group is blended with non-modified agarose.

Agarose is commonly used for separation techniques such as electrophoresis, Gel Permeation Chromatography, High Performance Liquid chromatography but also as a food additive. Recently the use of agarose hydrogel has shown to be useful for engineered ECM. Agarose has been successfully used to engineer cartilage de novo which suggest that further development will offer the possibility to regenerate other tissues. It has been shown that agarose gels induce bone reconstruction in vivo. It has also been shown that it is possible to modify the agarose backbone by oxidizing the primary alcohol group of the D-galactose residue in a highly regioselective manner. This modification enables grafting of molecules on the agarose gel through a carboxylic acid group. Therefore, the matrix of the present invention is highly valuable for biochemical and medical applications.

It has been observed that the oxidation of the C6 primary alcohol group of the D-galactose residue leads to a decrease of shear modulus but also to a weaker gel. The design of new material using agarose has been investigated by creating copolymer of agarose-collagen, or agarose-cellulose, but also by blending agarose with natural polymer of the ECM.

Modified agarose is the preferred component of the matrix of the present invention. It is however equally preferred that unmodified agarose is used as a matrix component. Moreover, it is possible to use other polysaccharides of natural origin as component which can be blended with modified agarose if such component cannot be oxidized as described above. If the structure of the polysaccharide contains a primary alcohol group which can be oxidized to a carboxylic acid group the repeating disaccharide units can be modified as described above in more detail for agarose. Other polysaccharides which can be used in the present invention are listed in Table 1 below. Polysaccharides in cells with bold borders comprise disaccharide units having a primary alcohol group. Therefore, these polysaccharides can be chemically modified in the manner described above. In particular, the polysaccharides used for the matrix of the present invention are hyaluronic acid, heparin sulfate, dermatan sulfate, chondroite sulfate, alginate, chitosan, pullulan, k-carrageenan. In the most preferred embodiment agarose is used.

In another embodiment of the present invention the matrix contains carrageenans in modified or/and unmodified form. Carrageenans are polysaccharides that are contained in red algae belonging to Gigartinaceae, Solieriaceae, Hypneaceae and the like. K-carrageenan, λ-carrageenan and η-carrageenan are known.

TABLE 1

| Name | Structure | Origin | Gelation Mechanism |
|---|---|---|---|
| Hyaluronic Acid | 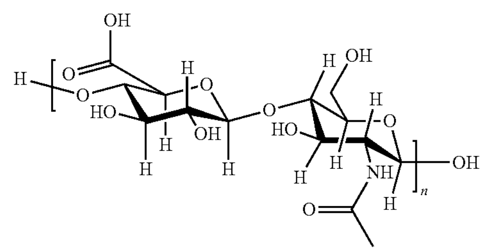 | Mammalian | use of crosslinker to for a 3D network |
| Heparin sulfate | 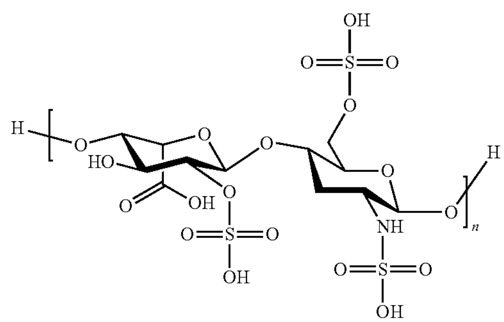 | Mammalian | |
| Dermatan sulfate | 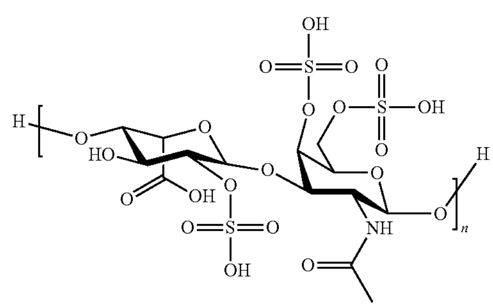 | Mammalian | |
| Chondroite sulfate | 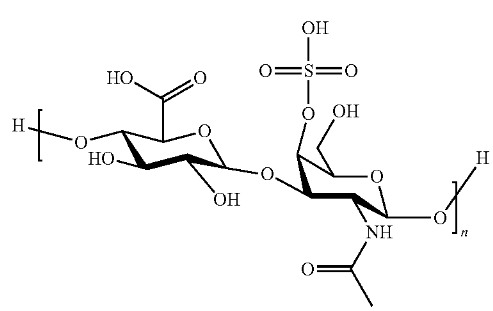 | Mammalian | |

TABLE 1-continued

| Name | Structure | Origin | Gelation Mechanism |
|---|---|---|---|
| Alginate | (structure) | Algae | Ca2+ bridges |
| Chitosan | (structure) | Marine shell | Repulsion of charges |
| Pullulan | (structure) | Fungus | Like cellulose, sheet organization |
| k-Carrageenan | (structure) | Algae | Helices aggregation |

In further preferred embodiments of the present invention the carboxylic group which is derived from the oxidation of the primary alcohol group is covalently coupled with a peptide sequence. In preferred embodiments the peptide sequence is selected from the group consisting of the cell adhesion sequence arginin-glycin-aspartic acid, the peptide sequences IKVAV (SEQ ID NO: 1) and YIGSR (SEQ ID NO: 2) or a protein which is preferably selected from collagen, collagen fragments, fibronectin and mixtures thereof. In yet another embodiment the protein sequence is vitronectin.

In another preferred embodiment the matrix may contain a modification of the carboxylic acid group derived from the oxidation of the primary alcohol group insofar that this carboxylic acid group is covalently linked to a nucleic acid sequence. The nucleic acid sequence may be single-stranded DNA, double-stranded DNA, single-stranded RNA and siRNA. The linkage between the carboxylic acid group and nucleic acid can be introduced by a method of click chemistry as known in the prior art. In case single-stranded nucleic acids are linked to the matrix, such single-stranded molecules may hybridize to complementary single-stranded molecules which are linked to other components. This offers the opportunity to easily attach molecules or even whole cells to the matrix.

Depending on the purpose of the use of the matrix it may be particularly helpful to include specific points of fixation into the matrix which can be designed according to the intended use of the matrix.

The present disclosure further describes the ability to change the tertiary structure of polysaccharides in a manner that the roughness, stiffness, thermal gelation behavior and optical feature of the material can be finely tuned to target a specific material, whereby the modification made on the backbone consists of an oxidation of the primary alcohol group of agarose backbone to the carboxylic acid group. It was demonstrated that this modification induces a change of organization of the polymer backbone and has been replicated in k-carrageenan as another polysaccharide. The gel of interest can be obtained by controlling the amount of chemical modification of the backbone but also by blending the native polysaccharide with the modified polysaccharide. This results in a uniform material with feature such as stiffness, thermal gelation and roughness that can be adjusted by incorporating different amounts of each polysaccharide.

The ease of control of the physical properties enables the design of an environment which is mechanically similar to natural human tissue but also biologically neutral since the agarose does not interact with cells. In case it is desired that cells interact with the material, biological ligands that are recognized by cells have to be grafted on the polymer backbone. Therefore two strategies have been followed; first the chemical way by using 1-(3-dimethylaminopropyl)-3-ethylcarbodiimide hydrochloride (EDC) coupling that allows direct chemical binding of the carboxylic acid group of the polysaccharide to the amine group on the N-terminus of a peptide. This process is illustrated in Scheme 2.

The peptide sequence can also be attached to the modified polysaccharide by click chemistry, whereby either azide or the alkyne moiety is coupled to the modified polysaccharide and the other moiety is coupled to the peptide sequence.

Scheme 2

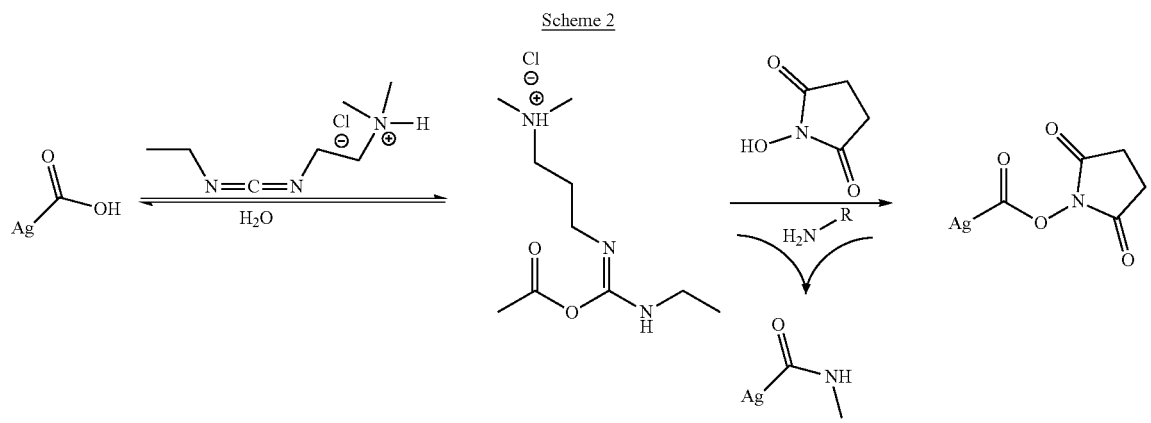

The second approach has been made with DNA coupling that enables an easier manipulation for the final user. An oligo-DNA strand can be coupled to the polymer backbone with the complementary oligo-DNA strand that has been previously chemically bound to the peptide of interest. This way of binding is for the final user a step forward to a fully tunable system, where the mechanical properties can be adjusted by mixing two components (native with modified polysaccharide) and the biological signal incorporated to the backbone polymer by adding a component to the system (the complementary oligo-DNA strand bounded to the peptide of interest). This principle is shown in FIG. 3.

In a preferred embodiment the matrix can be used as a scaffold of living cells in order to grow cells in a three-dimensional structure which resembles the natural environment. Cells, preferably human cells, which are preferably selected from the group consisting of chondrocytes, osteoblasts, osteoclast, skin epithelial cells, intestinal epithelial cells, corneal epithelial cells, astrocytes, neurons, oligodendrocytes, smooth muscle cells, endothelial cells, cardiomyocytes, pancreatic islet cells, kidney epithelial cells, embryonic stem cells, pluripotent stem cells; or naïve cells obtained from umbilical cord.

The matrix of the present invention can be further used for experimental purposes since the interaction of cells and its understanding gains more and more importance in many fields of biological research. Alternatively, the matrix can be used in order to produce artificial tissues. It is for example possible to grow the cells as described above in order to produce artificial three-dimensionally linked tissues which can be used as implant for the curing of various defects. It is for example possible to produce homologous bone structures by cultivating osteoblasts and/or osteoclasts in the matrix as described herein. Alternatively, artificial skin or cartilage can be produced. Since the material is well compatible with the immune system, no unexpected allergic reactions can be expected. This is especially true when homologous cells are used for the preparation of artificial tissues.

The matrix of the present invention can be implanted in mammalian body cavities both in the presence and in the absence of growth factors. These cavities can be with or without cells.

In a particularly preferred embodiment the matrix of the present invention is used as a regenerative implant. Such a regenerative implant is produced in vitro by using the matrix as a scaffold for the tissues which grow three-dimensionally in vitro. After the implant has reached the desired structure it can be implanted into a patient. Since the form of such an implant can be precisely designed by using the appropriate stiffness and viscosity or the required modulus usually in the first step the matrix is formed as a scaffold having the desired form. This matrix may be present in various forms. Sheets with a defined thickness are incubated with dermal cells and artificial skin can be produced thereby. Tubes having a well-defined diameter are incubated with suitable cells which form blood vessels like endothelial cells in order to produce artificial artherials or veins.

It is possible to form tubular structures which are brought into contact with such type of cells which form blood vessels. Alternatively, the matrix may have the form of a disc and the matrix will be brought into contact with cells which form cartilage tissues. Since the mechanical properties like stiffness, rigidity and viscosity of the matrix can be controlled by selecting the appropriate ratio of modified polysaccharide:unmodified polysaccharide, in particular modified agarose:unmodified agarose, the properties can be regulated very precisely. It is a further advantage of the present invention that the three-dimensional structure of the tissue is given by the matrix. Therefore, thickness, length or any other desired form of the matrix can be prepared by using a suitable form or mold. For medical purposes it is preferred to sterilize the agarose. This can be done either by appropriate chemicals or more preferred by heat treatment or by radiation.

The methods used to sterilize the agarose are not particularly limited. As a suitable chemical agent for sterilization ethylene oxide is advantageously used. Agarose can also be sterilized by a treatment with ionizing radiation, such as x-rays, γ-radiation or with electronic beam. It is however, particularly preferred to carry out sterilization of agarose by a heat treatment. Such heat treatment is advantageously carried out in an autoclave at a temperature of ca. 121° C. and pressure of 1.1 bar whereby the sterilization time of at least 15 min is required. Alternatively, sterilization can be carried out by a filtration using a sterile filter with pore size of less than 0.5 μm, preferably less than 0.3 μm.

After the matrix has been brought into the desired form and the form has been sterilized it is brought into contact with the desired cells, preferably in the appropriate medium which contains the desired growth factors. Depending on the type of cell which grows on the matrix, appropriate cytokines are added. It is also possible to add sequentially two different types of cells in order to form an matrix wherein tissues have been grown which resemble the part of the body which should be replaced or supported as far as possible.

Such matrices wherein tissue cells have been grown to form tissues can be used as regenerative implants in the treatment of humans. It is possible to produce by using the matrix of the present invention regenerative implants which can be used as artificial skin, as artificial blood vessels or for the replacement of nerve tissues. It is also possible to produce mucosal tissues or parts of the eye, in particular artificial lenses. A particular advantage of the present invention is that the matrix has superior optical quality which means that the matrix can be completely clear. In particular, a matrix containing a modified polysaccharide having a high modification degree has a particularly high transparency. This is extremely important for forming artificial cornea and/or lenses.

In another embodiment of the present invention the matrix can be used as a plastic surgery implant for reconstructive and cosmetic surgery in diverse body regions: in the facial region such as a nose, a forehead, a jaw, a cheek but also in a breast, a hip, a calf and the like. For example, in case of the nose correction, because the small implant is inserted between the nasal bone and the periosteum, the material of the implant need to be sufficiently stiff so that the implant does not deviate from its original position. However, in case of the breast correction, a relatively large implant and soft implant is employed.

The mechanical properties of the matrix such as stiffness and roughness can be adjusted as outlined above. Thus, the properties of the plastic surgery implant comprising the matrix can be conveniently adjusted depending on the intended purpose and used in a wide variety of body regions.

In yet another embodiment of the present invention the matrix can be used for producing controlled drug release formulations of pharmaceutically active components. By varying the mechanical properties of the matrix the controlled drug release formulation can be tailored to the desired purpose. If for example the matrix is very stiff, pharmaceutical agents which are included within the matrix will be delivered after implantation into the body very slowly. On the other hand, if the viscosity and the stiffness of the matrix are rather low, a pharmaceutical agent which is entrapped in the matrix will be released rather quickly.

In a further embodiment of the present invention the matrix can be used with pharmaceutically active agents like growth factors, insulin, biologically active peptides, chemokines, cytokines, steroids, antibiotics, analgethics and anti-inflammatory agents or anti-cancer drugs.

In a further embodiment the matrix can also be used for diagnostic purposes by including imaging agents as e.g. magnetic resonance imaging (MRI) contrast agents, computed tomography (CT) contrast agents, fluorescent imaging probes or radionuclei. By including those agents into the matrix and applying thereafter the matrix to the human body the agents are trapped into the matrix and can be released in a controlled manner by adjusting the properties of the matrix like viscosity, stiffness and form which depends on the intended use.

It is also possible to include into the matrix cells which form a tissue and pharmaceutically active agents.

Another embodiment of the present invention relates to the use of the matrix as a food additive. Such food additive is useful for the preparation of foods, drinks or seasonings. Preferably, the foods, drinks or seasonings contain 0.1 to 30 wt.-% of the matrix polysaccharide relative to the total weight of said food, drink or seasoning, more preferably they contain 0.5 to 25 wt.-% of the matrix polysaccharide, whereby the content of 1 to 20 wt.-% of the matrix polysaccharide is particularly preferred. The foods, drinks or seasonings containing the matrix of the present invention are not specifically limited. For instance, examples of such food include the following: products of processed cereal (e.g., wheat flour products, starch products, premixed puddings, jam, buckwheat noodle, wheat-gluten bread, jelly bears, gelatine noodle and packed rice cake), products of processed fat and oil (e.g., margarine, salad oil, mayonnaise and dressing), products of processed soybeans (e.g., tofu, miso and fermented soybean), products of processed meat (e.g. brawn and sausage), processed marine products (e.g., frozen fish, fish paste and fish fingers), dairy products (e.g., raw milk, cream, yogurt, butter, cheese, condensed milk, powdered milk and ice cream), products of processed vegetables and fruits (e.g., paste, jam, pickle), and the like.

Because the components of the matrix have a sufficient chemical stability, the process for producing the food, drink or seasoning containing the matrix of the present invention is not limited to a specific one. Any processes including cooking, processing and other generally employed processes for producing a food, drink or seasoning can be used and the components of the matrix may be added before, during or after the cooking or processing, either separately or in a form of a pre-prepared matrix.

Importantly, the amount as well as the properties of the matrix employed producing the food, drink or seasoning can be adapted according to the desired consistency of the resulting products. For instance, preparation of jelly bears typically requires a higher content of the matrix polysaccharides than preparation of a pudding.

The matrix of the present invention can also be used as a pharmaceutical excipient, for instance for the preparation of oral pharmaceutical formulations.

In another embodiment the matrix of the present invention is used as a component of cosmetic compositions such as make-up, blush, lipstick, eyeshadow, antiperspirants, deodorants and concealer. The cosmetic compositions comprise 0.1 to 50 wt.-% of matrix polysaccharide, preferably 0.5 to 30 wt.-% of matrix polysaccharide, even more preferred 1 to 25 wt.-% and particularly preferred 2 to 20 wt.-%. The content of matrix polysaccharide is chosen according to the desired mechanical properties of the cosmetic compositions. Preferably, the cosmetic compositions are characterized by being single phase.

Preferably, the cosmetic compositions are solid or semi-solid at temperature of 25° C. and have such a consistency that they can be molded into the form of a stick. For this purpose, the compositions can be heated until molten and then poured into a mold and cooled. Alternatively, the compositions are capable of being formed into sticks, but are poured into pans or other types of cake or cream forms to deliver certain consumer benefits. For example, an eyeshadow composition may be molded in the stick form, but usually it is desired to pour it into a pan for a more convenient use from a consumer standpoint.

The physical properties of the resulting cosmetic compositions can be conveniently adjusted by an appropriate choice of the matrix components and by their amount in the composition.

In another embodiment the matrix of the present invention is used as a material for industrial purposes, in particular as for dispersion control, for conditioning of liquids and as a lubricant. Because the properties of the matrix, such as stiffness and temperature of gelation can be conveniently tuned by adapting the modification degree of the modified polysaccharide, their matrix of the present invention is suitable for a wide range of industrial applications.

The concentration of the polysaccharide components of the matrix in the aqueous solution typically ranges from 1 to 4 wt.-%, particularly preferred from 1 to 3 wt.-%. In a particularly preferred embodiment the concentration of the polysaccharide components of the matrix in the aqueous solution ranges from 1 to 2 wt.-%. It is even more preferred that this concentration is about 2 wt.-%.

The aqueous solution can further contain other compounds, such as salts or proteins, in particular water-soluble proteins.

Preferred Embodiments of the Invention

Modified agarose is prepared from agarose by a synthetic protocol known from the prior art. NaOH solution is added to the reaction mixture during the reaction in order to maintain the optimal pH of 10.8 of the reaction mixture and neutralize the carboxylic acids being formed. As oxidant (2,2,6,6-Tetramethyl-piperidin-1-yl)oxyl (TEMPO) is used, which in turn, is reactivated with sodium hypochloride NaOCl and in the presence of potassium bromide KBr as a catalyst (Scheme 1). The addition of NaOH further allows following the reaction progress, and gives a quantitative characterization of the amount of carboxylic acid formed as it compensates the formation of the acidic moiety.

Thus, a relationship between the volume of the added NaOH solution and the ratio of the disaccharide repeat units in which the primary alcohol group was oxidized to the carboxylic acid group ($DPI_{Agarose}$) is described by the Equation 1.

$$\frac{m_{Agarose}}{M_{n_{Agarose}}} \times DPI_{Agarose} = n_{NaOH}, \quad (1)$$

wherein
$m_{Agarose}$ is the mass of the agarose,
$M_{n_{Agarose}}$ is the number average molecular weight of the agarose used as a starting material, and
$n_{NaOH}$ is the amount of the added NaOH solution.

At the end of the oxidation reaction sodium borohydride $NaBH_4$ is added to the reaction mixture. Thus, the aldehyde groups resulting from an incomplete oxidation of the primary alcohol groups are reduced back to the primary alcohol groups.

In order to have precise and reliable result, the oxidation reaction was followed by several different techniques. As a first qualitative analysis the samples of the reaction mixture were lyophilized and analyzed by $^{13}C$ MAS-NMR. The obtained $^{13}C$ MAS-NMR spectra show the appearance of a peak at 180 ppm, characteristic for the carbonyl carbon atom of carboxylic acid groups, and the vanishing of the peak at 55 ppm which is characteristic for the carbon atom of the primary alcohol group (FIG. 4C).

Infrared spectrometry FTIR was used as a quantitative method. The FTIR spectra of the reaction mixture show the increase of the ratio between the peaks at 1650 $cm^{-1}$: vibration band of the double bond carbon-oxygen (C=O) of the carboxylic acid group and 1360 $cm^{-1}$: the vibration band of the bond carbon-oxygen (C—OH) of the primary alcohol group (FIG. 4B). The relative amounts of the carboxylic acid groups and of the primary alcohol groups can be calculated by integrating the peaks of interested and using the Equation (2).

$$\% \text{ Oxidation} = \frac{\int V_{C=O}}{\int V_{C=O} + \int V_{C-OH}} \times 100, \quad (2)$$

wherein
$\int V_{C=O}$ is the area under the C=O absorption peak,
$\int V_{C-OH}$ is the area under the C—OH absorption peak and
% Oxidation is the conversion grade of the oxidation reaction.

The formation of carboxylic acid groups along the polysaccharide backbone was also monitored by measuring the amount of the NaOH solution consumed during the oxidation reaction and afterwards by the quantitative analysis using FTIR spectrometry. In order to compare both analytical methods, the amount of NaOH solution added to the reaction mixture was plotted against the calculated conversion grade determined by FTIR. A linear relationship between these values confirms the accuracy of both analytical methods and verifies the reproducibility of the oxidation reaction (FIG. 4D).

It is assumed that the incorporation of ligands at the primary alcohol groups of the C6 position on the D-galactose of the agarose repeating unit leads to a lower shear modulus (G') and a lower temperature of gelation. In order to investigate in which manner the introduction of carboxylic acid groups on the polysaccharide backbone induces the change of mechanical and gelation properties the authors of the present invention conducted a systematic rheological study of the gels.

The gelation point, also named temperature of gelation, is determined by the equality of the shear storages to the loss moduli at a constant shear frequency and deformation with decreasing the temperature as shown in FIG. 5A. In comparison to the technique of the inverted bottle the temperature sweep is an objective measure that gives a more precise value. As can be readily recognized from FIG. 5C an increase of modification degree of a polysaccharide lowers its gelation temperature in a linear way. In particular, the gelation temperature of native agarose is 40° C. (not shown in FIG. 5C), while the gelation temperature of modified agarose having 93% modification is 5° C.

This phenomenon can be used for tuning of the gelation temperature of the gel in order to adapt it to a particular application. Therefore, also the gelation temperature of the matrix of the present invention can be efficiently tuned by adjusting the modification degree of the modified polysaccharide.

Moreover, the agarose forms a hydrogel that has a hysteretic behavior, i.e. the formation of physical crosslinked points happened at a lower temperature than the breakdown of the gel. This feature of the gel leads to an improved thermal stability of the corresponding matrix, and makes it a promising material for biological applications.

The gel stiffness can be characterized by doing a frequency sweep, shear of the gel at a constant deformation and temperature with a frequency increase. In rheology a gel state can be defined as state where the shear and loss moduli are both independent on the shear frequency, FIG. 5C. The modification of the polysaccharide backbone induces a lower shear and loss moduli which results in a weaker gel. This weakening of the polymer network seems to be related to the incorporation of carboxylic acid groups, as the loss of primary alcohol groups results in a linear loss of stiffness (FIG. 5D).

The versatile stiffness of these gels can be compared to the human tissue stiffness. Moreover, the values of the shear modulus of the matrix of the present invention are also comparable to those of human tissues. The shear modulus of the cell surrounding has been reported to vary from $10^5$ Pa for bones down to $10^1$ Pa for nerves. The order of magnitude of the gel stiffness covered by the different proportion of modification ranges from $10^4$ Pa for a 2% w/v gel of native agarose to $10^2$ Pa for a 93% modified gel of the same concentration. Thus, adaptation of the modification degree of the modified polysaccharide allows an efficient adaptation of the resulting ECM for a wide range of human tissues.

It is known that the agarose backbone folds in an α-helix and that the gel is formed by the aggregation of these helices. The loss of rigidity of the different gels for a given concentration could be attributed to a loss of aggregation of the α-helix. Moreover, the loss of the gel turbidity attributed to the amorphous structures formed by the aggregates reinforces the hypothesis of a loss of crosslinked point (FIG. 5E).

It has been suggested in the literature that the physical crosslinked point formed in the agarose hydrogel can be assimilated as spherical nanoparticles and then be characterized with static light scattering (SLS). It appears that the increase of the modification degree along the polymer backbone dramatically decreases the size of this crosslinked point and also their polydispersity resulting in smaller aggregates of a smaller size distribution, see FIG. 6F. These results support the hypothesis of less aggregation of α-helix, but the loss of polydispersity is also a quantification of the organization of the aggregate. The decrease of the polydispersity reveals that the aggregates are organized in a more regular shape.

On the other hand, the measurement of the zeta-potential gives information of the mobile charges present on the polymer surface. It appears that the increase of the modification is linearly proportional to the increase of the zeta potential, see FIG. 6E. The increase of the zeta-potential transcript the incorporation of repulsion charges between the polymer chains that might disrupt the aggregation of the α-helix domains.

In the past, the α-helix of the agarose has been characterized by using circular dichroism (CD) spectroscopy. The native agarose CD spectrum is composed of a single peak at 185 nm that is characteristic for an α-helix conformation of the secondary structure. In order to understand the gelation mechanism of the modified agarose, CD has been measured for several modified agarose preparations having different degrees of modification. It appears that the peak characteristic for an α-helix is shifted to higher wavelength and a new peak appears at 203 nm, see FIG. 6A. The hypothesis of a lower number of α-helix aggregate will have lead to a reduced ellipticity in the α-helix area of the spectrum, but the shift of the spectrum to another area suggest a change of the folding of the modified agarose.

The analogy of the conformation of polysaccharides with the folding of proteins gives an indication of the new secondary structure of the modified agarose. Indeed, the peak in the area of 203 nm corresponds to the organization of proteins in β-sheet. The consistent study of different modified gels highlights that the appearance of the new peak is linearly proportional to the amount of carboxylic acid groups along the polysaccharide backbone, see FIG. 6C. The modification of the primary alcohol group to the carboxylic acid group clearly induces a change of the secondary structure into the agarose that is still able to form a gel at low temperature.

The CD spectrum of the modified agarose has been measured at two different temperatures, at 5° C. where the modified agarose is below its sol-gel transition temperature and at 90° C. above its gel-sol transition temperature. It appears that at high temperature the new peak at 203 nm vanishes. The modified agarose forms a gel that is temperature dependent, whereby the temperature dependency of the new peak suggest that the gel dependency is now driven by this new organization and not anymore by the aggregation of the α-helix.

Importantly, agarose is not the only polysaccharide which exhibits an α-helix structure. Indeed members of the carrageenan family, for instance κ-carrageenan are also known to organize in α-helices and also to form physical gels that are temperature-dependent.

The authors of the present invention carried out the same spectroscopy study to characterize the k-carrageenan that has been oxidized at the same position, according the same protocol than the agarose. The peak of the unmodified k-carrageenan and unmodified agarose are of opposite sign due to the different helix rotation, but both of them are in the same wavelength. The CD curves obtained for the modified k-carrageenan exhibit the same new peak at the same wavelength of 203 nm, see FIG. 6D. The possibility to obtain the same CD behavior for two polysaccharide of the same family implies that the modification of this primary alcohol groups in theses polymers can be a general method to induce a β-sheet like structure in polysaccharides.

In order to validate these hypotheses a molecular dynamic (MD) simulation of two polysaccharides backbones over 15 ns was ran. Past studies on polysaccharide have demonstrated the relevance of the MD simulation. It is of high importance to validate the model of the new organization of the modified agarose. The root mean square deviation (RDSD) of the geometry from its initial position shows that after 2 ns a stable conformation is obtained. Importantly, this conformation remains stable until the end of the simulation, see FIG. 7A. In order to characterize the distance between the two polysaccharides strands the formation of hydrogen bond (H-bond) between these two strands has been calculated. The formation of an H-bond is driven by the distance of an electronegative atom to a hydrogen atom. Each H-bond on each frame has been summed and this sum has been plotted against the time. Therefore a stable H-bond sum transcript the non presence of any H-bond, see FIG. 7B.

This calculation shows that the native agarose is able to form H-bond all along the simulation, but the totally modified agarose strands do not form any H-bonds after 5 ns, highlighting that the two polymer chains are too far from each other in order to interact together in this manner. The non interaction of the two polymer strands confirms the data obtained from the zeta potential that show repulsion forces between the two strands.

The main question that has to be answered by the simulation is the physical and geometrical possibility to form a β-sheet structure. In past studies the conformation of the sugar cycles of the polymer chain has been analyzed using a Ramachandran plot. The dihedral angle of the glycosidic linkage can be plotted and compared with the cartography obtained for protein folding. The native agarose has its dihedral angle formed by the anhydro-galactopyranose/galactose bound of the chain 1 and galactose/anhydrogalactopyranose bound of the chain 2 in the α-helix domain, see FIG. 7C. The same bounds on the modified agarose have their dihedral angles in the β-sheet area of the plot, see FIG. 7D. The change of area of the dihedral angles that switch from the α-helix position, to the β-sheet location show that this suggested organization from the other analysis is possible.

The animations created by the software give an idea about the polymers chains position along the time of the simulation. The conformation of the polymer of the first frame has been obtained from the X-ray data of the agarose. The two polymers have been modeled with the same initial conformation. It appears that the chains of the native agarose are staying together along the simulation time, but the chains of the modified agarose are repulsed from each other and position their carboxylic acid groups opposite to each other.

Thus, the MD simulation attests the possibility of this β-sheet conformation. As for the CD data, the plot of the dihedral angles is based on the theory developed for proteins. The use of the specific area of the Ramachandran plot in order to describe the folding of protein has only been used so far, for proteins. As the organization of the chains of polymer changes from an aggregation of α-helix to a β-sheet, the impact on the macrostructure of the material should be non negligible.

The authors carried out an investigation of the macrostructure of the gel by using environmental scanning electron microscopy (ESEM), see FIGS. 8A-8F, A1 to D1. The highest difficulty in the study of gels is the difficulty to reveal the hydrated structure of the polymer network. Therefore freeze dried sample have been used for the ESEM. The change of structure between the native and the modified agarose shows a radical change of their structure. The unorganized fibers of the native agarose leave the place to a highly ordered fibril structure as the percentage of modification of the polymer backbone is increased. The unorganized fibers are coupled with small ordered area in the 28% modified sample. The 60% modified gel is more organized and reveals still small domains of unorganized fibers, but the 93% modified gels is totally organized in sheets.

In summary, the authors of the present invention found that the modification of a polysaccharide leads to a change of its tertiary structure.

This new organization of polysaccharide is surprising. The images obtained by the authors validate the hypothesis of a new folding structure but moreover confirm the β-sheet organization of the polymer chains. The CD spectroscopy showed that the modification of the primary alcohol groups of the D-galactose of the agarose repetition unit leads to the same change of folding of the secondary structure.

The structure of the k-carrageenan hydrogels was imaged by following the same protocol as for the agarose. The ESEM image reveals that the modification of the k-carrageenan primary alcohol groups leads to the same highly organized structures forming thin sheets of the same kind as for 93% modified agarose gels.

In summary, the authors showed for two different polysaccharide of the same family that the same change of organization takes place when primary alcohol groups are oxidized to carboxylic acid groups. These results encourage the possibility of a general method for modifying polysaccharide organization and predicting their secondary structure based on the protein models already existing, see FIGS. 8A-8F, A4, A5, D4 and D5.

Cells which are cultivated on two-dimensional substrate show a dependence on the roughness of the substrate. Therefore the surface of the gel has been characterized in a semi-dry state by using atomic force microscopy (AFM). AFM can reveal the roughness of the surface. The height pictures highlight a loss of the relief, as the modification is increased, see FIGS. 8A-8F, from A2 to D2. The tri-dimensional reconstruction allows visualizing clearly the loss of the roughness, see FIGS. 8A-8F, from A2 to D2. The mathematic calculation of the roughness of the gel surface appears to be linearly related to the amount of carboxylic acid on the polymer backbone, see FIG. 8F.

The loss of the roughness can be explained by the smaller crosslinked points, aggregates calculated with the light scattering experiment, that are formed in the modified gels. The surface is smoother and the organization in sheets shown by the ESEM correlates with the explanation of a smoother gel that has fibers which are more organized in a unilateral direction.

DESCRIPTION OF THE DRAWINGS

FIGS. 8A-8E. FIG. 8A: native polysaccharide, FIG. 8B: 28% of modification, Row 1 is the ESEM of 2% w/v freeze dried agarose gel; Row 2 is the AFM of the height of agarose gels, Row 3 is the 3D reconstruction of AFM pictures. FIG. 8C: 60% of modification, FIG. 8D: 93% of modification Row 1 is the ESEM of 2% w/v freeze dried agarose gel; Row 2 is the AFM picture of the height of agarose gels, Row 3 is the 3D reconstruction of AFM pictures, FIG. 8E: Row 1 is the ESEM of 2% w/v freeze dried k-carrageenan gels at low magnification; Row 2 is the ESEM of 2% w/v freeze dried k-carrageenan at high magnification.

EXAMPLES

Figure 1:
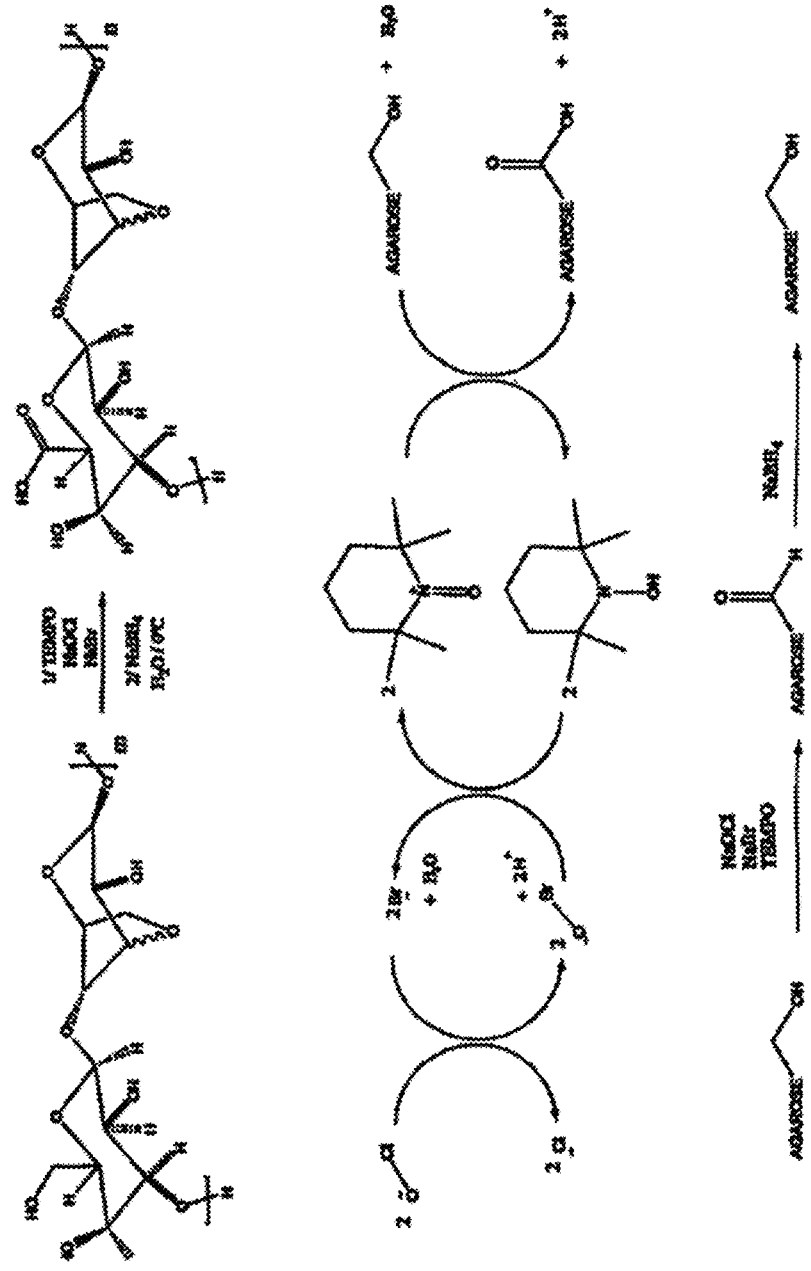
FIG. 1 shows a mechanism for polysaccharide modification.
Figure 2A:
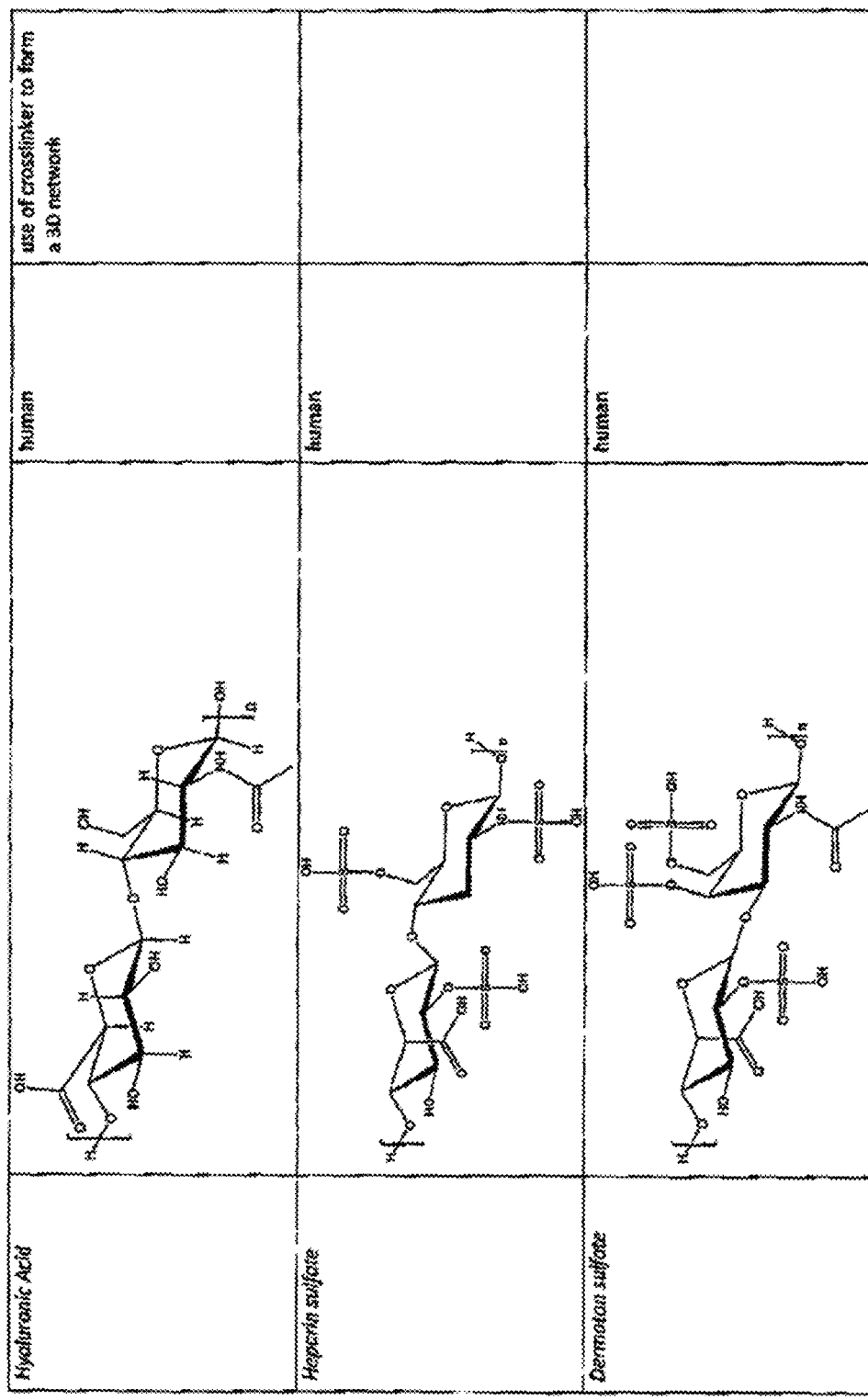
FIGS. 2A-2C shows examples of polysaccharides.
Figure 2B:
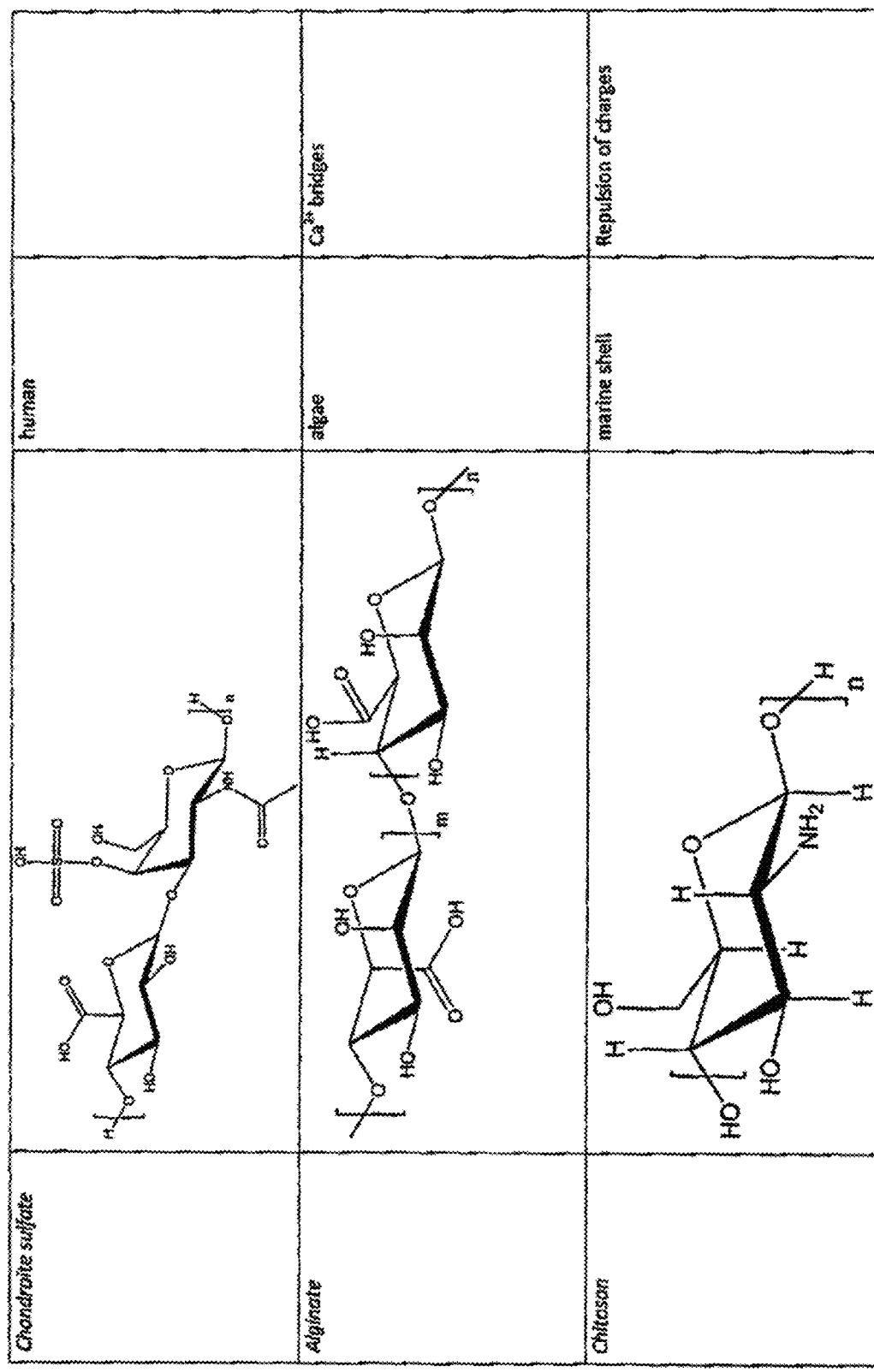
Figure 2C:
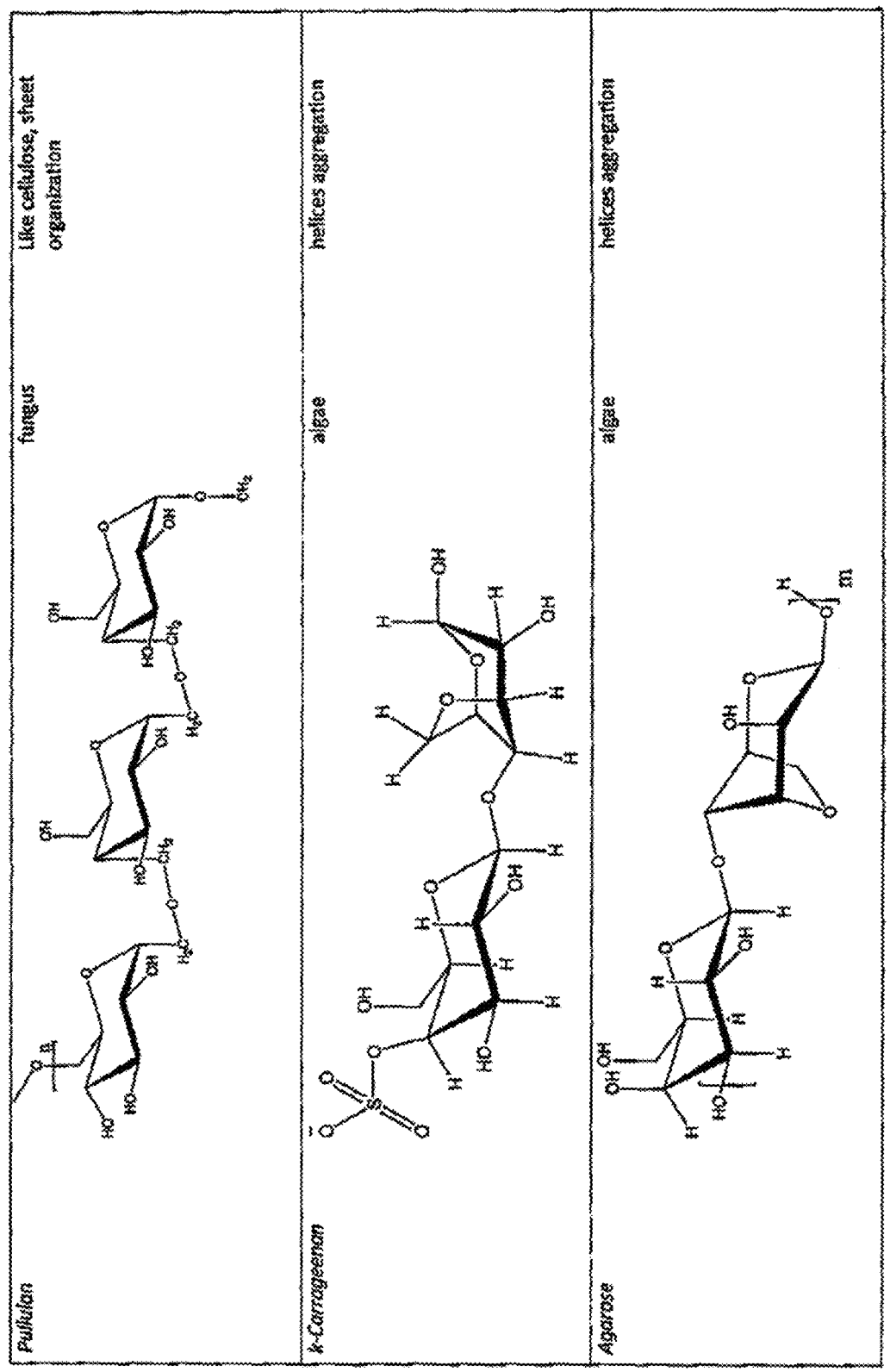
Figure 3:
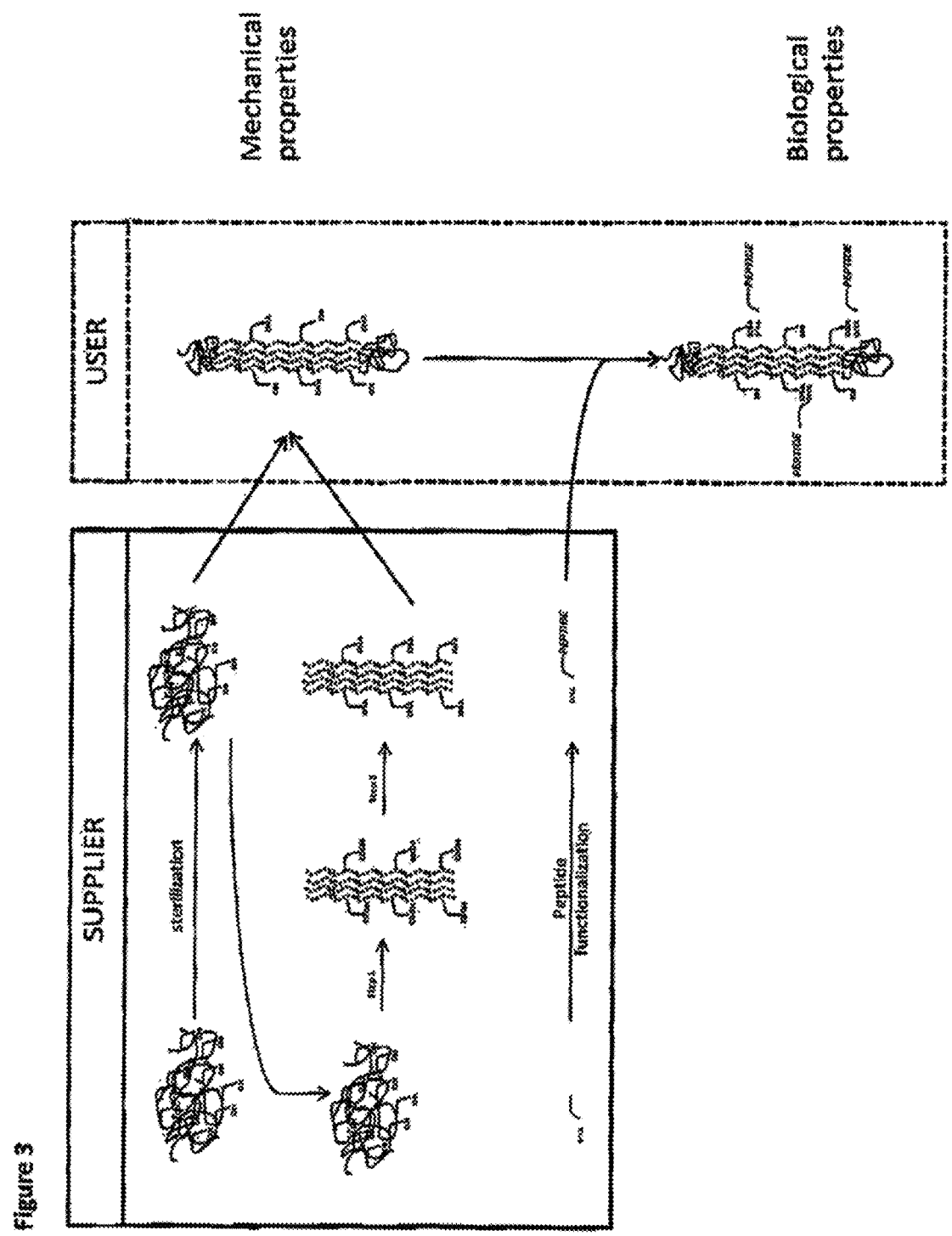
FIG. 3 shows a scheme illustrating the strategies for preparation of modified polysaccharides. In the box on the left hand side modifications made by the supplier are shown. In the box on the right hand side two blendings made by the final user are represented.
Figure 4A:
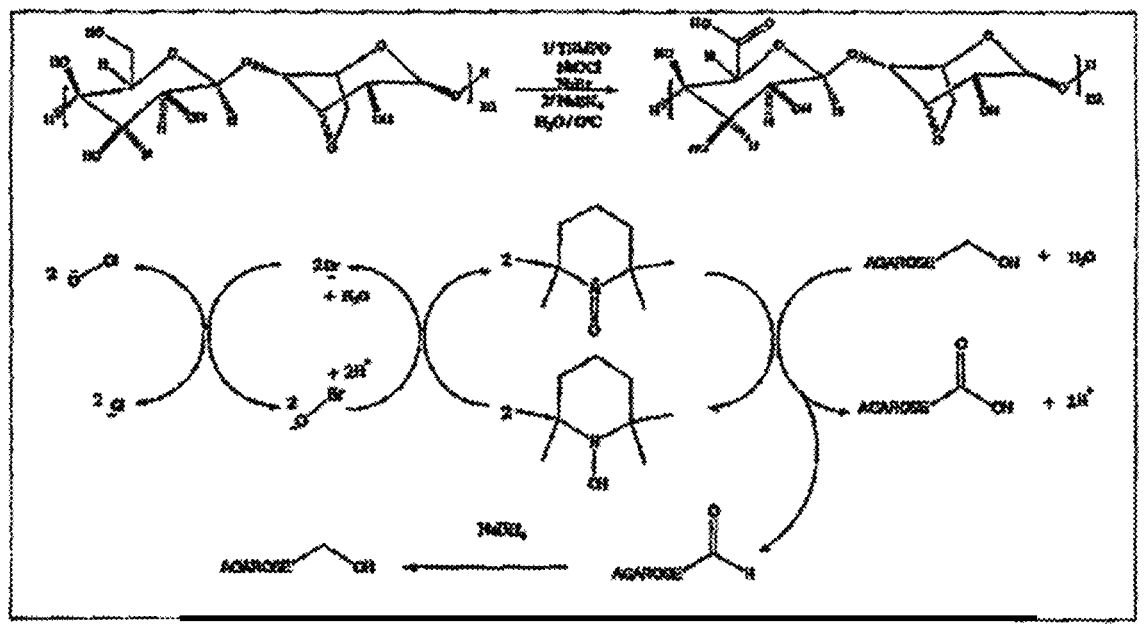
FIG. 4A shows a reaction mechanism of D-Galactose primary alcohol oxidation into a carboxyl acid.
Figure 4B:
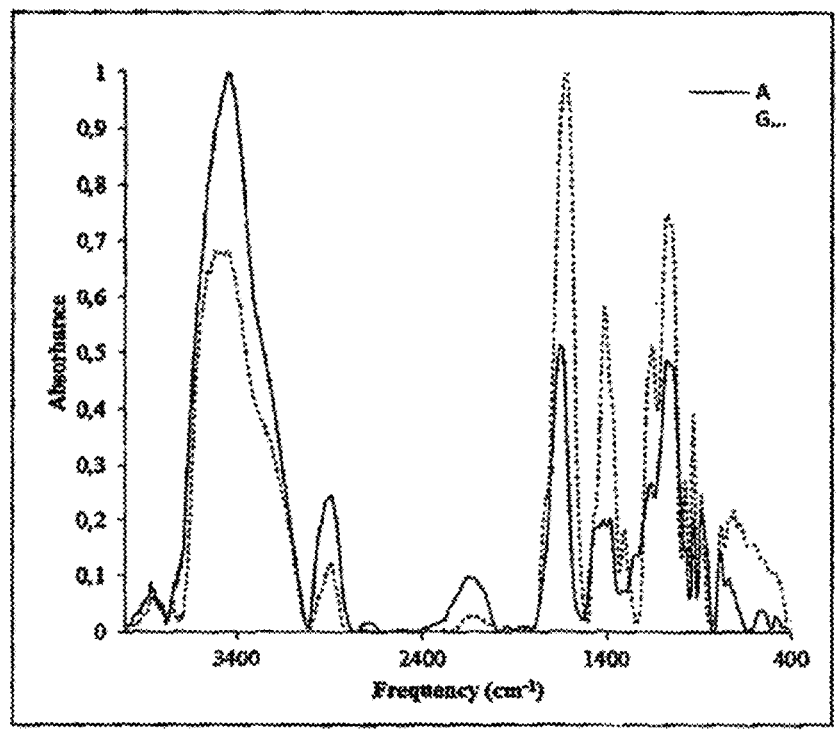
FIG. 4B shows FTIR spectra of the modified agarose (solid line) and the native agarose (dotted line).
Figure 4C:
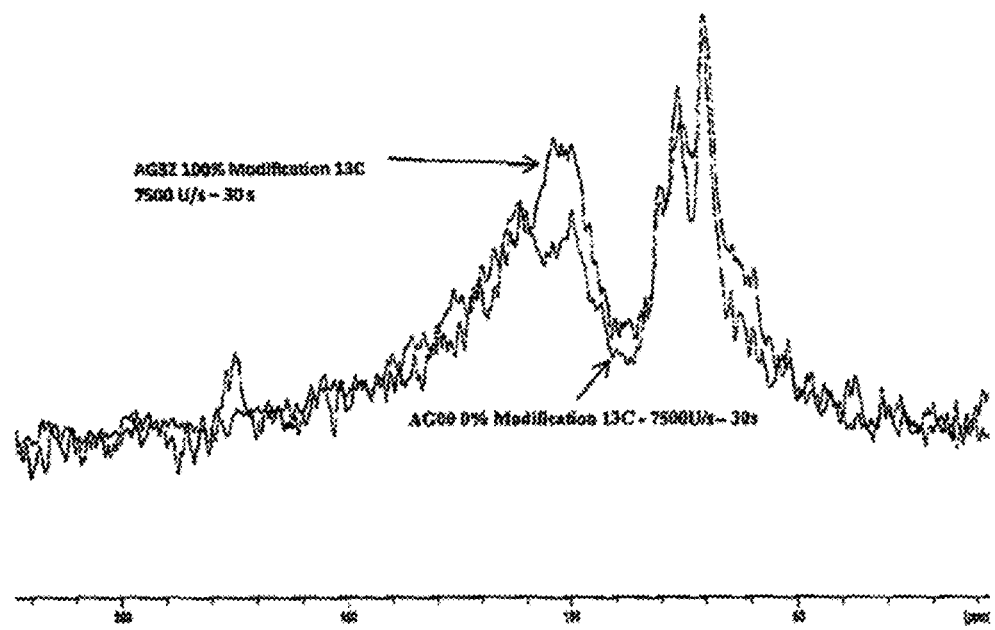
FIG. 4C shows $^{13}$C-MAS-NMR spectra of the modified agarose (black) nad the native agarose (grey).
Figure 4D:
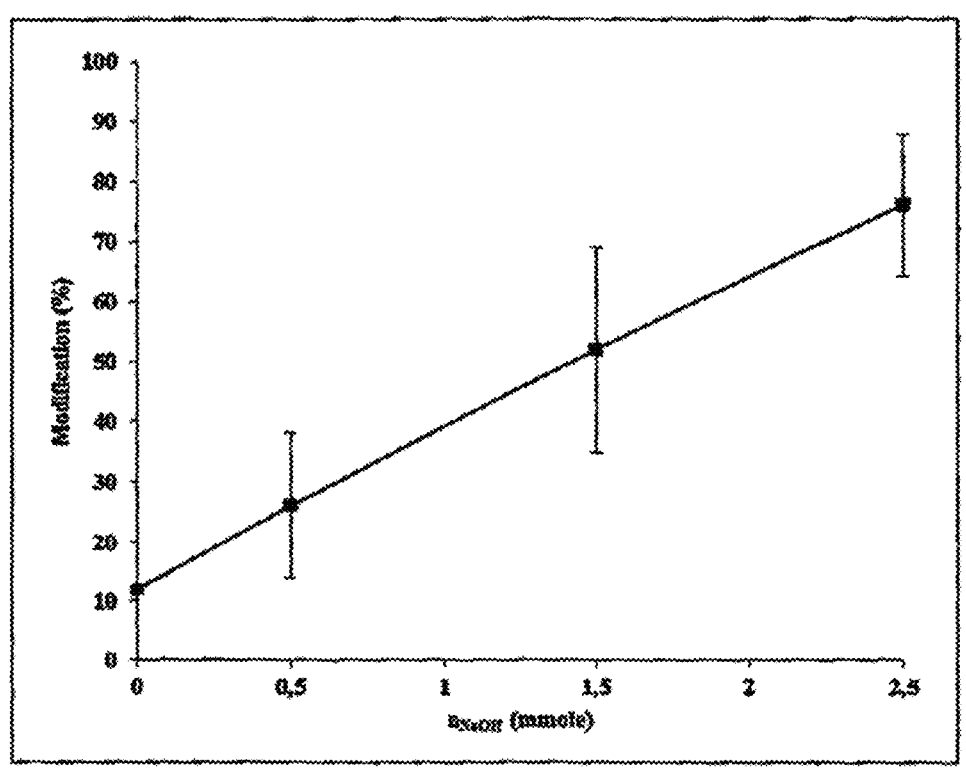
FIG. 4D is a plot of the percentage of modification as determined by FTIR against the amount of NaOH solution added to the reaction mixture as a mean of 12 reactions. Error bars represent the standard deviation.
Figure 5A:
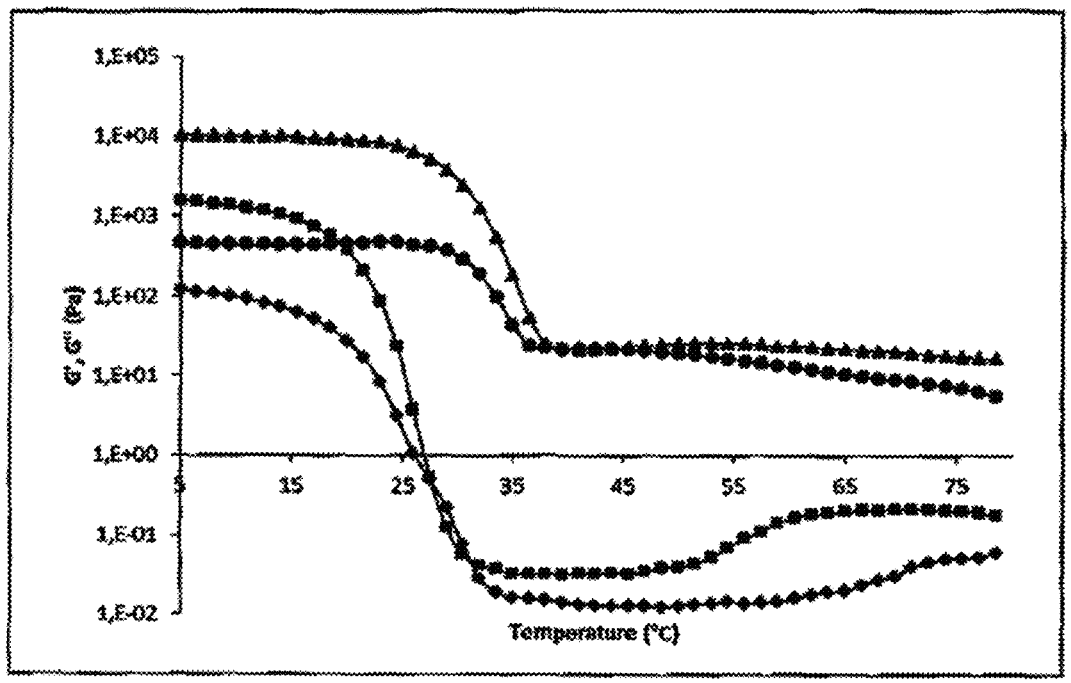
FIG. 5A shows a temperature sweep of native agarose (black) and 60% modified agarose (squares and rhomboids), squares and rhomboids represent G' and triangles and squares represent G".
Figure 5B:
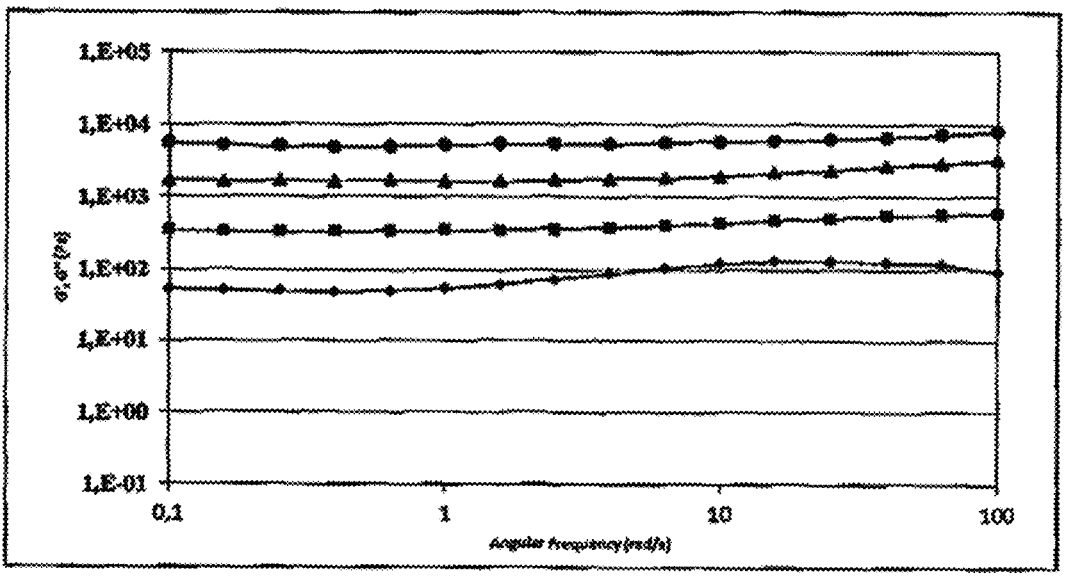
FIG. 5B shows a frequency sweep of native agarose (dots and triangles) and 60% modified agarose (squares and rhomboids), dots and rhomboids represent G' and triangles and squares represent G".
Figure 5C:
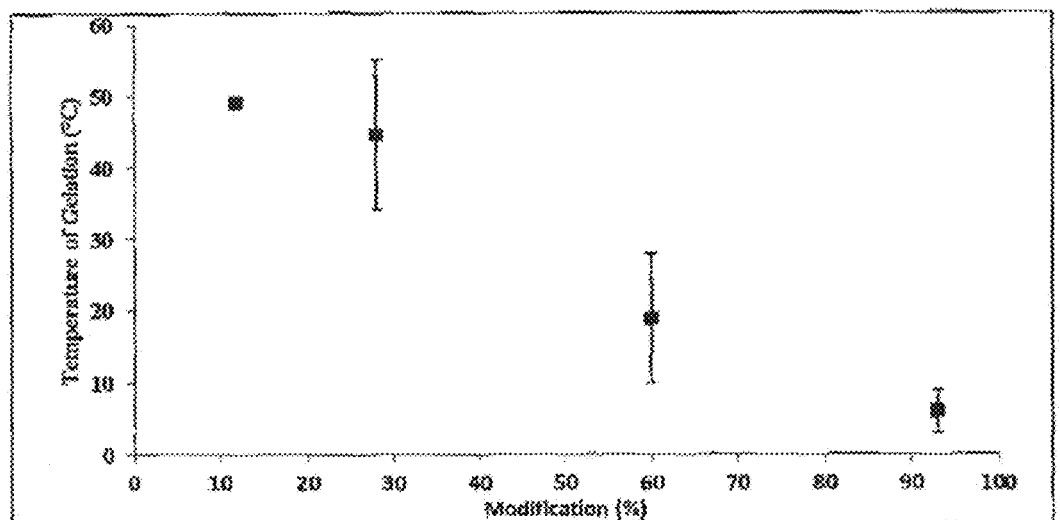
FIG. 5C represents a plot showing the relationship between the temperature of gelation of modified agarose and the percentage of its modification. The error bars represent the standard deviation.
Figure 5D:
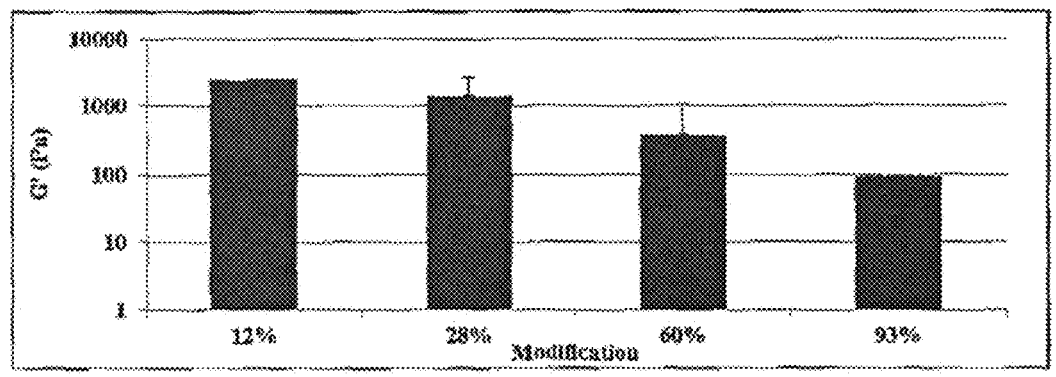
FIG. 5D is a diagram showing the shear modulus G' of agarose samples having different percentage of modification. The error bars represent the standard deviation.
Figure 5E:
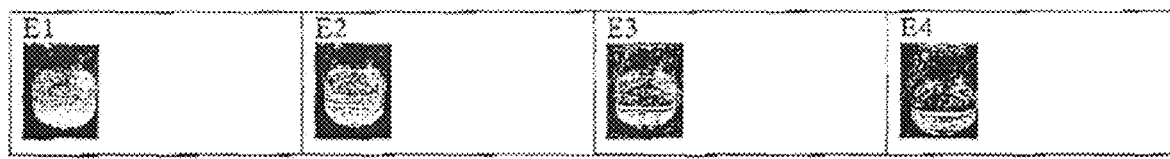
FIG. 5E Photographs of gels containing 2% w/v respectively: 1: 93% modified agarose; 2: 60% modified agarose; 3: 28% modified agarose; 4: native agarose.
Figure 6A:
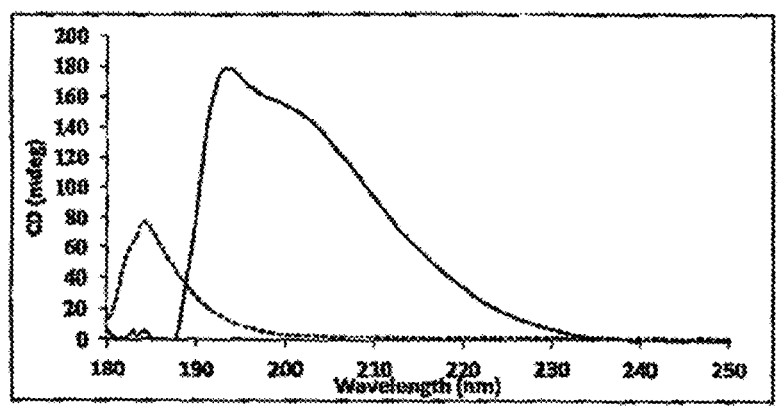
FIG. 6A shows a CD spectrum of native agarose (black) and 93% modified agarose (grey).
Figure 6B:
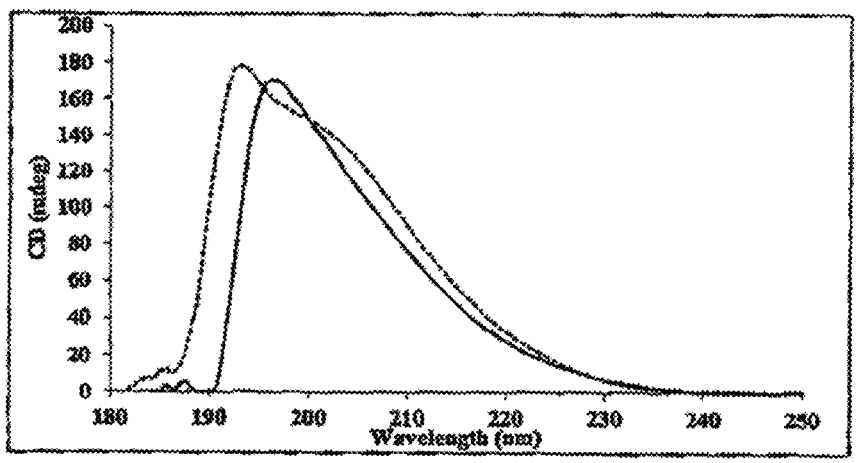
FIG. 6B shows a CD spectrum of 93% modified agarose at 5° C. (dashed) and 93% modified Agarose at 90° C. (solid).
Figure 6C:
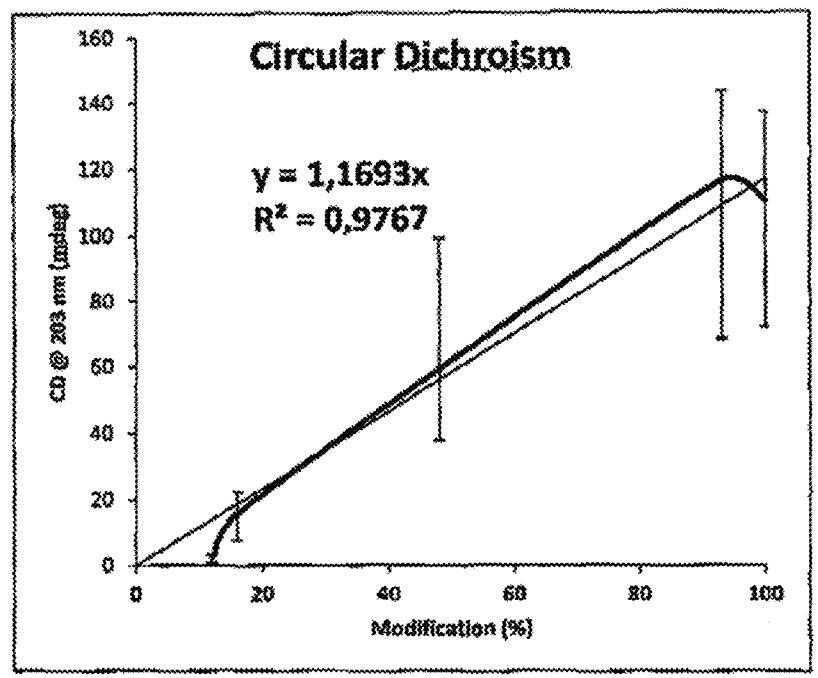
FIG. 6C shows CD of agarose gels having a different degree of modification of at 203 nm. Error bars represent the standard deviation.
Figure 6D:
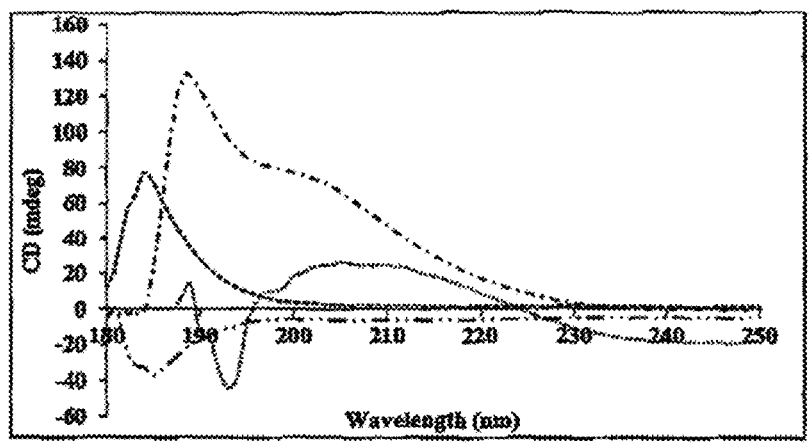
FIG. 6D shows CD spectra of native agarose (dashed), 93% modified agarose (dashed; one point), native k-carrageenan (dashed; two points), 93% modified k-carrageenan (dotted).
Figure 6E:
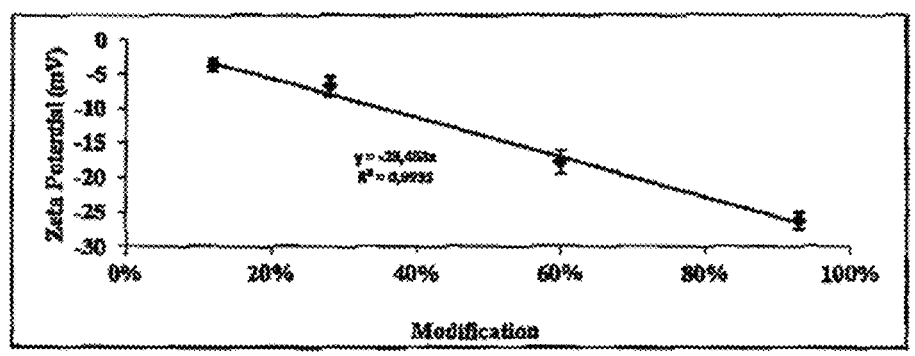
FIG. 6E shows a plot of zeta potential (mV) of modified agaroses vs. their degrees of modification. Error bars represent the standard deviation.
Figure 6F:
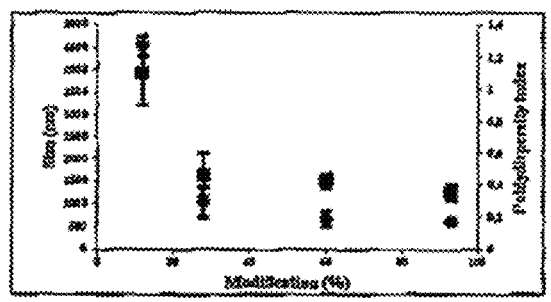
FIG. 6F shows plots of polydispersity (black) and size (grey) measured by light scattering of diluted solutions of different modified agaroses vs. their degrees of modification. Error bars represent the standard deviation.
Figure 7A:
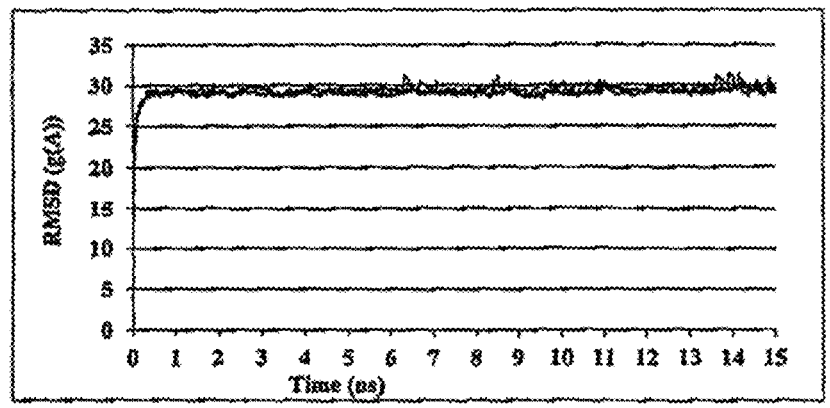
FIG. 7A shows a RMSD from the first frame for native agarose (black) and 100% modified agarose (grey).
Figure 7B:
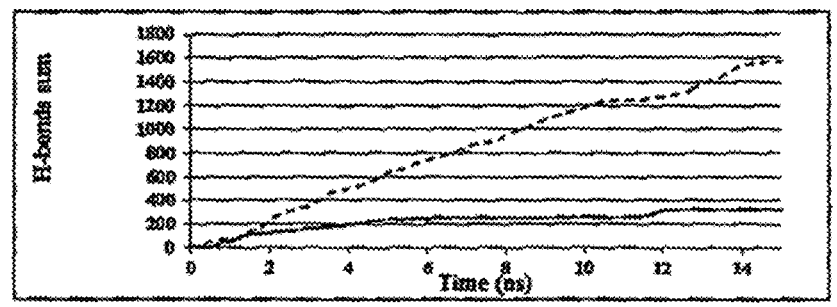
FIG. 7B represents the sum of cumulated H-bonds between the two strand of polysaccharide during the MD simulation for native agarose (dashed) and 100% modified agarose (solid).
Figures 7C, 7D:
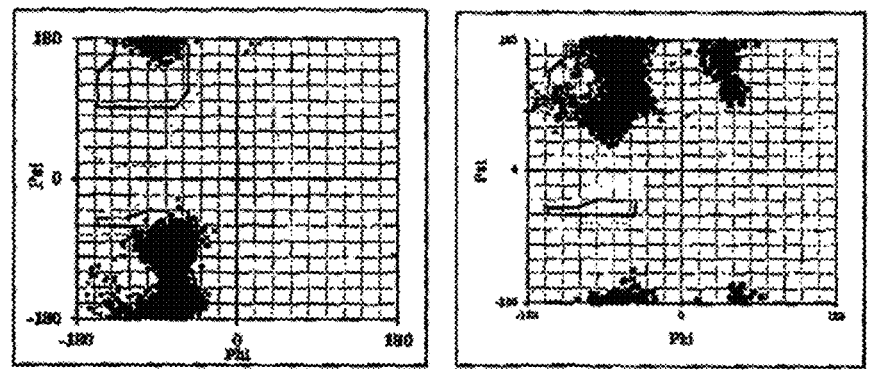
FIG. 7C shows a Ramachandran plot of native agarose AG link in chain 1 and GA link in chain 2.
FIG. 7D shows a Ramachandran plot of totally modified agarose AG link chain 1 and GA link in chain 2.
Figure 7E:
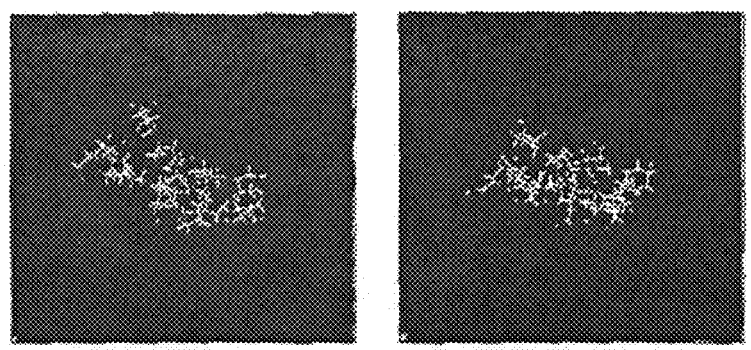
FIG. 7E shows the MD simulation for native Agarose (left) and from the middle of the simulation (right).
Figure 7F:
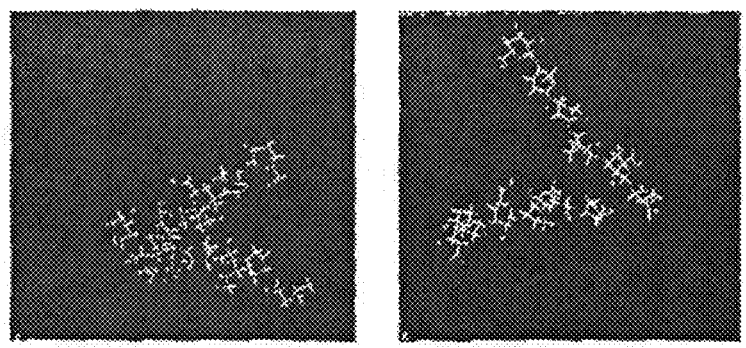
FIG. 7F shows the MD simulation for totally modified Agarose (left) and from the middle of the simulation (right).
Figures 8A, 8B:
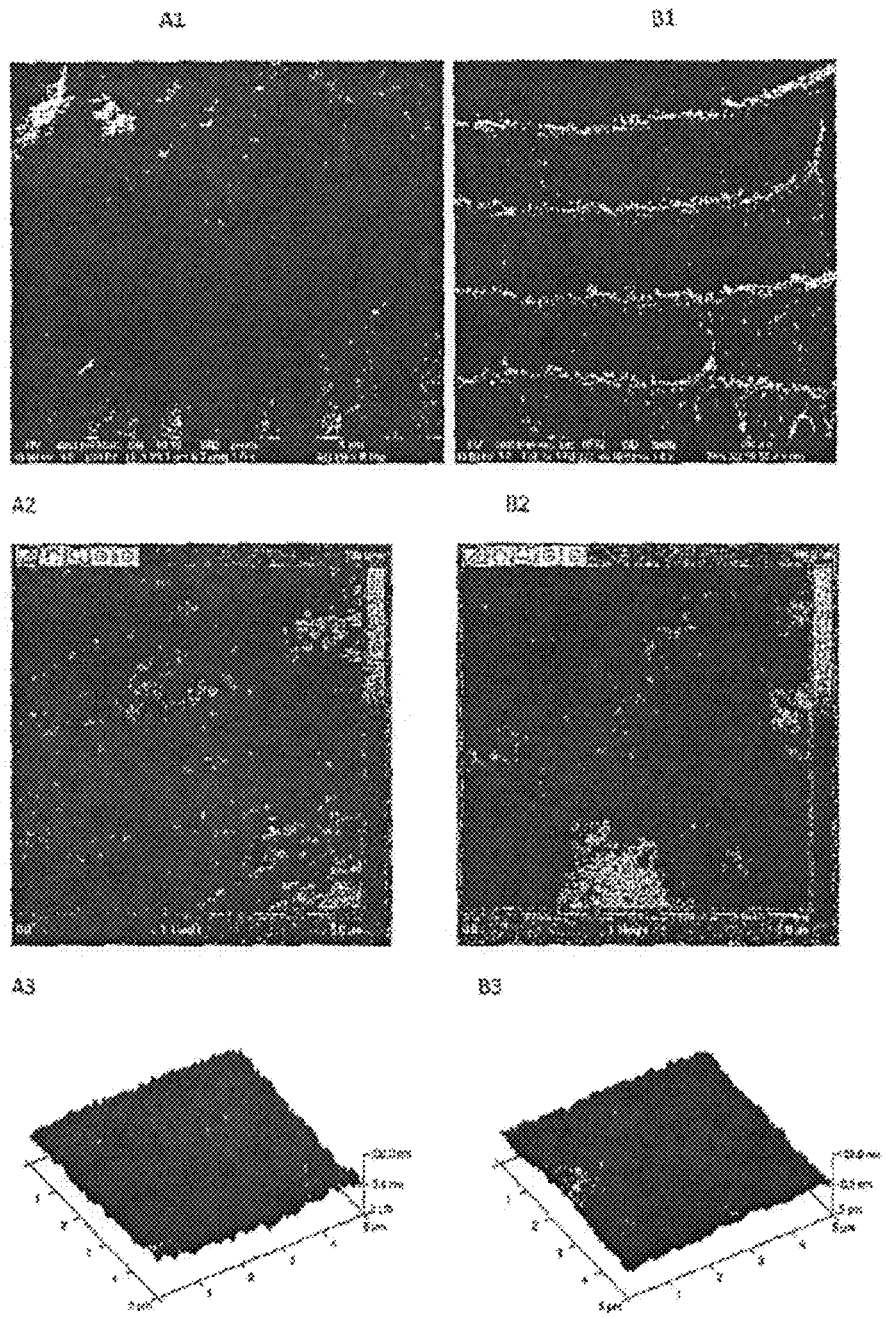
Figure 8E:
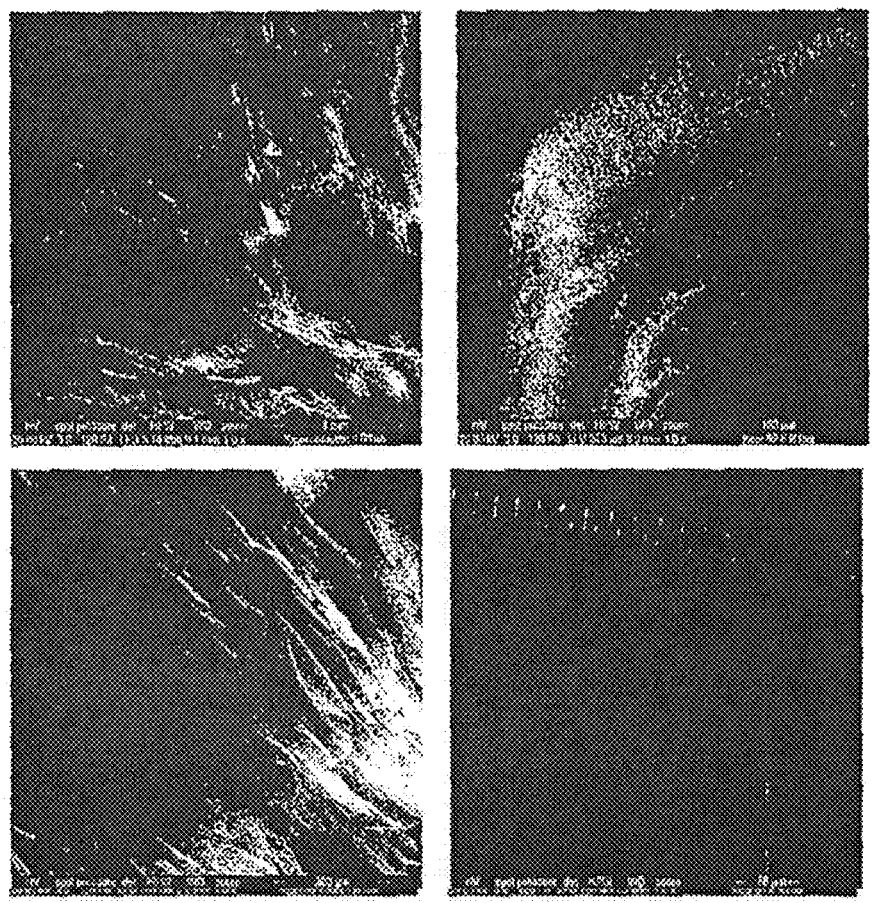
Figure 8F:
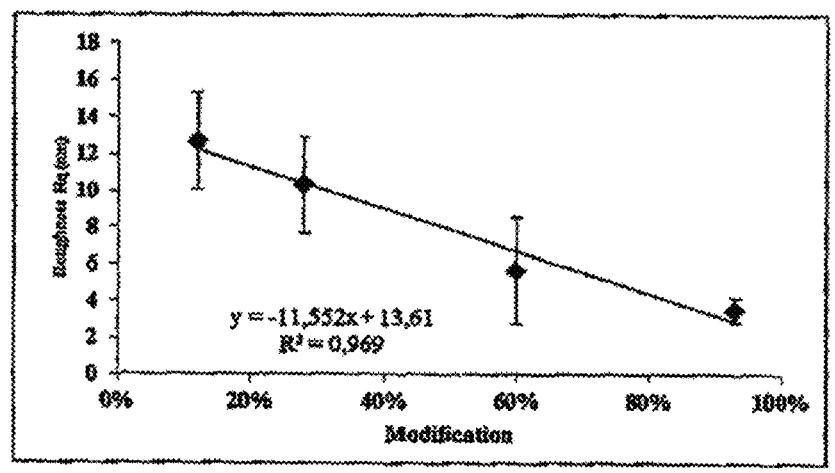
FIG. 8F is a diagram showing the surface roughness of the AFM sample of agarose gels plotted against the percentage of modification.

The following non-limiting examples will illustrate representative embodiments of the invention in detail.

Methods Description a) Infrared Spectroscopy

FTIR spectra have been recorded on a Brucker Vector 22 FT-IR spectrometer in KBr pellets at 20° C. The pellets were prepared with 2 mg of the substance in 200 mg of KBr, then grinded and pressed under a pressure of 10 tons press for 10 min.

b) Nuclear Magnetic Resonance

Magic Angle Spinning NMR spectra were recorded at room temperature (20° C.) in the solid state using a Brucker Avance DRX 500 spectrometer. For this purpose freeze dried samples were put in a ceramic holder and spined at 7500 U/s.

c) Rheology

Rheology experiments were performed with a MCR rheometer Anton Paar Physica MCR 301 equipped with a Peltier temperature cell. Sample were prepare as 2% w/v in deionized water, heated at 90° C. and stirred for 10 min until a clear solution was obtained. The liquid was then poured on the rheometer plate, pre-heated at 80° C., using a pipette. The solution was allowed to stabilize for 10 min before the recording was started. A plate tool from Anton Paar: PPR25 was used for all experiments. Sol-gel transition and frequency sweep were made using the same sample in a single cycle: 10 min equilibrium at 80° C., cooling down to 5° C. in 30 min and record of G' and G" every 1.5° C. at 1 rad/s with a deformation of 10%, stabilized at 5° C. for 30 min, heated up at 37° C. and stabilized for 30 min then the frequency sweep was recorded at 37° C. by increasing the rotation frequency from 0.01 rad/s up to 10 rad/s over 30 min with a deformation of 10%. Sol-gel transition temperature was calculated as the temperature where $\tan \theta = 0$.

d) Circular Dichroism

Circular dichroism spectra were obtained using a Jasco J-810 spectropolarimeter equipped with a Peltier temperature cell Jasco PFD-425S. Solution of 0.15% w/v of agarose was made in Milli-Q water at 90° C. for 15 min then solution have been cooled down to 5° C. in the CD chamber for 30 min prior measurement. Each spectrum was recorded three times and the obtained spectra were summed together. Each spectrum for a given modification is a mean of three batches obtained by three different syntheses.

e) Dynamic Light Scattering

Dynamic light scattering (DLS) measurements were carried out on a Beckman Coulter Delsa™ Nano C particle analyzer with a polystyrene cuvette of 1 cm. Agarose was dissolved in Milli-Q water at 90° C. for 15 min to obtain a 0.15% w/v solutions that was cooled down at room temperature for a day. The light scattering was done at 15° C. and samples were equilibrated for 30 min prior to measurement. For each value three measurements were done and an average was calculated. Each point is a mean of three batches obtained by three different syntheses.

f) Zeta Potential

Zeta potential was measured on a Beckman Coulter Delsa™ Nano C particle analyzer. The same solutions were used as for the light scattering experiment. Measurements were made in a flow cell that was aligned with the laser prior every measurement. Each measurement was made three times and an average was calculated. Each spectrum for a given modification is a mean of three batches obtained by three different syntheses.

g) ESEM

ESEM images were obtained with a ref agarose gels. 2% w/v solutions were prepared and 2 ml of these solutions were freeze-dried for 24 hours under 0.1 mbar vacuum in a 5 ml glass vial. The samples were vertically cut and the inside of the sample was imaged at different magnification. Images shown here are representative images of different areas of a given sample at different magnification, which were reproduced with three different gels prepared from different batches.

h) AFM

AFM images were obtained with a scanning probe microscope Veeco Dimension 2100. The samples were prepared on a 3 mm microscopic glass holder that was previously passivated. The glass slide was washed with 0.1 M NaOH solution and dried in the oven. The dry slides were then passivated with a few drops of dichloromethylsilane. Two slides were sandwiched together to have a uniform passivation. After 10 min the slides were washed with water and the excess of dichloromethylsilane was washed away with soap after what the slides were dried. Slides side was prepared in a hydrophobic way. Agarose samples were prepared as 2% w/v gels and 25 µl of the obtained solution was poured on an unmodified glass slide. A dichloromethylsilane passivated slide was then adjusted on top of the solution. Slides of 0.5 mm were put as spacers between the hydrophobic and the normal glass slide, the whole montage was then allowed to gel for 30 min at 4° C. The upper slide (hydrophobic) was after that removed and a thin layer of agarose gel was obtained. This gel was then allowed to stabilize at room temperature for 30 min before measurement in order to avoid any shrinkage or dilatation of the gel during the measurement.

i) Molecular Dynamic Simulations

MD simulations were done using the Desmond package of the Maestro, Version 8.5 from Schrödinger. Initial conformation was been obtained from the X-ray structure of the agarose that was downloaded from the protein database (PDB) library. Modified agarose was drawn from the PDB file directly inside the Maestro software. Implicit water model was build using the Desmond tool, resulting in a 10 Å square box build by following the TIP3 solution model. The simulations were run in the model NPV at 300° K at atmospheric pressure for 15 ns. Analysis of the results was done using the VMD software and the tools available in the standard package.

j) Elementary Analysis

Samples have been analyzed on an element analyzer Elementar Vario EL

Example 1

Modification of Agarose

Agarose type I was obtained from Calbiochem. (2,2,6,6-Tetramethylpiperidin-1-yl)oxyl (TEMPO), NaOCl, $NaBH_4$, NaBr, 1-ethyl-3-(3-dimethylaminopropyl)carbodiimide (EDC) and 2-(N-morpholino)ethanesulfonic acid (MES) buffer were obtained from Sigma Aldrich and used as received. Solution of 0.5 M NaOH as well as solution of 5 M HCl were freshly prepared every three-month. Ethanol technical grade was used without any further purification. Deionized water was used for non-sterile synthesis.

Agarose was modified under sterile conditions: all the chemicals were dissolved in autoclaved water and filtered with a 0.2 µm filter. All the glassware was autoclaved and the reaction was conducted under a laminar flow. Agarose (1 g) was autoclaved in MilliQ water. Autoclaved agarose was poured into a 3 necked round bottom flask, which was used as a reactor. A mechanical stirrer was adapted to one of the neck. A pH-meter was adapted another neck of the round bottom flask. The reaction mixture was then cooled down to 0-5° C. and vigorously stirred. TEMPO (0.160 mmol, 20.6 mg) was added, NaBr (0.9 mmol, 0.1 g) and NaOCl (2.5 ml, 15% solution) was as well poured inside the reactor. The resulting solution was adjusted to pH=10.8 with HCl and NaOH solution. The pH was maintained at 10.8 by adding NaOH solution. At the end of the reaction $NaBH_4$ (0.1 g) was added and pH=8 was reached. The solution was stirred for 1 hour and NaCl (0.2 mol, 12 g) and ethanol (500 ml) was added. The agarose was precipitated and extracted in a funnel. The two layers were then filtered on a frit glass. The agarose was then dialyzed in Spectra Pore 4 membranes, MWCO=12-14000 for 2 days and the water was changed two times. Prior dialysis, the membranes were left overnight in a 70% ethanol solution, 2 hours before use they were rinsed in autoclaved water. Finally, the product was put on a freeze-drier Christ LD 2-8 LD plus at 0.1 mbar for the main drying and at 0.001 mbar during the desorption phase. Samples were put in round bottle flask and freezed in liquid nitrogen bath on a Rotary evaporator modified for this purpose. Thin layer of frozen solution was obtained on the flask wall reducing the lyophilization time.

Example 2

Modification of K-Carrageenan

K-carrageenan was obtained from Sigma Aldrich and used as such. K-carrageenan was objected to a TEMPO-mediated oxidation, according to the synthetic protocol of Example 1.

The resulting modified k-carrageenan was dialyzed and freeze-dried, as specified in Example 1 above.

Example 3

Blending of Modified Agarose with Unmodified Agarose

Blends of modified agarose and native agarose in different proportions were prepared. The resulting blends were studied using CD spectrometry. The obtained results indicate that the blending of two polysaccharides lead to the same change in tertiary structure as the modified polysaccharide. This suggests that these two polysaccharides are miscible and can be used for engineering new matrices.

The rheology studies show a specific behavior of the gel. Indeed the blended gels have a higher shear modulus than the unmodified gel of agarose. These results suggest that the organization of the modified chains with the unmodified chains follows a new mechanism, that is different from modified agarose.

The ESEM image illustrates the structure of the gels and reveals a different organization of the fibers than for the unmodified agarose. As well for the surface roughness, the roughness of the blended gels is not dependent of the proportion suggesting a new mechanism of organization.

Example 4

Covalent Biding of Peptide to Modified Agarose

Peptide GGGGRGDSP (SEQ ID NO: 3) was obtained from Peptide International.

Functionalization of agarose with the $G_4$RGDSP peptide (SEQ ID NO: 3) was done by EDC peptide coupling. Agarose (30 mg, 0.25 µmol) was dissolved in autoclaved water; all the chemical and buffer were sterilized on a 0.2 µm filter, MES buffer was added and the solution reached a pH=4. The peptide (500 µg) was added thereto, followed by EDC (200 mg) and the resulting solution was stirred for two hours at 40° C. to avoid any gel formation. The solution was then dialyzed in Spectra Pore 4 MWCO=12-14 kDa, whereby water was changed three times. Subsequently, the sample was freeze-dried. Prior dialysis the membranes were left overnight in a 70% ethanol solution, 2 hours before use they were rinsed in autoclaved water.

Example 5

Use of Modified Extracellular Matrix for Biological Tests

Cell Culture:

Modified gels were prepared at a 2% w/v concentration in DMEM media and heated at 60° C. for 30 minutes in order to avoid any degradation of the RGD peptide. The temperature was adjusted to 37° C. and the culture media was completed with usual nutrients and cytokines. Human chondrocytes were obtained from ATCC and used between passage 3 and 5. Solution of agarose was mixed with the cells and then seeded in a 48 wells plate. The plate was then stored at 4° C. for up to 30 min in order to allow the sol-gel transition to occur. The plates were then cultivated in a incubator at 37° C., 4% $CO_2$ for two weeks.

Cell Shape Factor:

All images were taken on an Axio Observer A1, from Carl Zeiss, equipped with a differential interference contrast (DIC) filter. The images were taken after 1, 5 and 14 days at different magnification in different area of the sample. The cell perimeter and cell area were then measured and the cell shape factor (CSF) was calculated. The results are a mean of three different batch of peptide modified agarose which was reproduced two times, which represent a total of 6 wells. Per well more than 100 cells were measured in order to have a meaningful CSF.

Real Time PCR:

At 7 days, 14 days and 21 days of cell culture in the gel, the media was removed and the gels were frozen at −80° C. overnight. The solids obtained were then crushed and digested with a CT AB buffer. Then extract using the Qiagen kits.

The invention claimed is:

1. A method, comprising:
performing plastic surgery on a subject by injecting, into the subject, a modified agarose, wherein at least 11% of the modified agarose exhibits a β-sheet structure.

2. The method of claim 1, wherein the modified agarose further comprises a pharmaceutically active agent.

3. The method of claim 1, wherein the modified agarose comprises a carboxylated agarose.

4. The method of claim 1, wherein the modified agarose has a shear modulus G' in the range of from 10 Pa to $10^7$ Pa.

5. The method of claim 1, wherein the injection further comprises an unmodified polysaccharide.

6. The method of claim 5, wherein the unmodified polysaccharide comprises agarose.

7. The method of claim 5, wherein the unmodified polysaccharide comprises one or more of a member of the carrageenan family, hyaluronic acid, heparin sulfate, dermatan sulfate, chondroitin sulfate, alginate, chitosan and pullulan.

8. The method of claim 1, wherein the modified agarose is obtained by oxidizing at least one primary alcohol group in at least 11% of an unmodified agarose.

9. The method of claim 1, wherein 20% to 99% of the modified agarose exhibits a β-sheet structure.

10. The method of claim 1, wherein 50% to 95% of the modified agarose exhibits a β-sheet structure.

* * * * *

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ile Lys Val Ala Val
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Tyr Ile Gly Ser Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gly Gly Gly Gly Arg Gly Asp Ser Pro
1               5